US009539327B2

(12) United States Patent
Pincus et al.

(10) Patent No.: US 9,539,327 B2
(45) Date of Patent: Jan. 10, 2017

(54) SMALL MOLECULE CANCER TREATMENTS THAT CAUSE NECROSIS IN CANCER CELLS BUT DO NOT AFFECT NORMAL CELLS

(75) Inventors: Matthew R. Pincus, Brooklyn, NY (US); Josef Michl, Little Neck, NY (US); Ehsan Sarafraz-Yazdi, New York, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 1220 days.

(21) Appl. No.: 12/744,831

(22) PCT Filed: Nov. 26, 2008

(86) PCT No.: PCT/US2008/084810
§ 371 (c)(1),
(2), (4) Date: Dec. 9, 2010

(87) PCT Pub. No.: WO2009/070650
PCT Pub. Date: Jun. 4, 2009

(65) Prior Publication Data
US 2011/0183915 A1 Jul. 28, 2011

Related U.S. Application Data

(60) Provisional application No. 60/990,276, filed on Nov. 26, 2007.

(51) Int. Cl.
A61K 31/155 (2006.01)
A61K 45/06 (2006.01)
A61K 31/4995 (2006.01)
A61K 38/10 (2006.01)
A61K 38/17 (2006.01)
A61K 47/48 (2006.01)
C07K 14/47 (2006.01)

(52) U.S. Cl.
CPC ............ *A61K 45/06* (2013.01); *A61K 31/155* (2013.01); *A61K 31/4995* (2013.01); *A61K 38/10* (2013.01); *A61K 38/1709* (2013.01); *A61K 38/1758* (2013.01); *A61K 47/48023* (2013.01); *C07K 14/4746* (2013.01); *C07K 2319/03* (2013.01)

(58) Field of Classification Search
CPC .................................................. A61K 31/155
See application file for complete search history.

(56) References Cited

U.S. PATENT DOCUMENTS 5,519,118 A 5/1996 Vogelstein et al.
5,550,023 A 8/1996 Kinzler et al.
5,618,921 A 4/1997 Burrell et al.
5,702,908 A 12/1997 Picksley et al.
5,770,377 A 6/1998 Picksley et al.
6,063,911 A 5/2000 Vournakis et al.
6,153,391 A 11/2000 Picksley et al.
6,310,040 B1 10/2001 Bozyczko-Coyne et al.
6,326,464 B1 12/2001 Conseiller et al.
6,492,116 B1 12/2002 Chene et al.
6,617,346 B1 9/2003 Kong et al.
6,734,302 B2 5/2004 Kong et al.
6,784,157 B2 8/2004 Halazonetis et al.
6,897,197 B2 5/2005 DePinho
6,962,792 B1 11/2005 Ball et al.
7,083,983 B2 8/2006 Lane et al.
7,132,421 B2 11/2006 Fotouhi et al.
7,138,236 B1 11/2006 Jackson et al.
7,173,006 B2 2/2007 Mukherjee et al.
7,241,738 B2 7/2007 Averback et al.
2002/0031818 A1 3/2002 Ronai et al.
2002/0077283 A1 6/2002 Sessa
2002/0098581 A1 7/2002 Glassy et al.
2003/0104622 A1 6/2003 Robbins et al.
2003/0109437 A1 6/2003 Averback et al.
2004/0038902 A1* 2/2004 Pincus ........................... 514/14
2004/0110690 A1 6/2004 Bonny
2005/0090646 A1 4/2005 Sullivan
2005/0137137 A1 6/2005 Lane et al.
2005/0215548 A1 9/2005 Wang et al.
2005/0245451 A1 11/2005 Pincus
2006/0105956 A1 5/2006 Pincus et al.
2006/0211757 A1 9/2006 Wang et al.
2006/0258841 A1 11/2006 Michl et al.
(Continued)

FOREIGN PATENT DOCUMENTS

WO 98/47919 A1 10/1998
WO 03/105880 A1 12/2003
WO WO2005/123676 * 12/2005

OTHER PUBLICATIONS

Virkajarvi et al. APMIS, 105; 765-772, 1997.*
Vasslilev (J Medicine Chemistry 2005 vol. 48, No. 14, pp. 4491-4499).*
Futaki, Shiroh et al., "Arginine-rich peptides an abundant source of membrane-permeable peptides having potential as carriers for intracellular protein delivery", The Journal of Biological Chemistry, vol. 276, No. 8, issue of Feb. 23, pp. 5836-5840, 2001.
Okuyama, Masahiro et al., "Small-molecule mimics of an α-helix for efficient transport of proteins into cells", Nature Methods, vol. 4, No. 2, pp. 153-159, 2007.

(Continued)

*Primary Examiner* — Amber D Steele
(74) *Attorney, Agent, or Firm* — Hoffmann & Baron, LLP

(57) ABSTRACT

A method of treating cancer in a subject, including: providing a subject having a plurality of cancer cells; and administering to the subject, a therapeutically effective amount of a composition including: an HDM-2 binding component; and a membrane resident component, the membrane resident component bound to the HDM-2 binding component. Also provided are a method of selectively necrosing cancer cells, a method of causing membranolysis in cancer cells, and a cancer treatment composition.

3 Claims, 13 Drawing Sheets

(56) References Cited

U.S. PATENT DOCUMENTS

| | | |
|---|---|---|
| 2007/0238666 A1 | 10/2007 | Pincus |
| 2008/0076713 A1 | 3/2008 | Pincus |
| 2010/0143358 A1* | 6/2010 | Weisbart ............... 424/134.1 |

OTHER PUBLICATIONS

Bowne, Wilbur B., et al., "Novel peptides from the RAS-p21 and p53 proteins for the treatment of cancer", NIH Public Access, vol. 5B, pp. 331-344, 2007.

Schaschke, N., et al., "Epoxysuccinyl peptide-derived cathepsin B inhibitors: modulating membrane permeability by conjugation with the C-terminal heptapeptide segment of penetratin", Biological Chemistry, vol. 383, No. 5, pp. 849-852, 2002. (abstract).

Fischer, Peter M., et al., "Small-molecule inhibitors of the p53 suppressor HDM2: have protein-protein interactions come of age as drug targets?", TRENDS in Pharmacological Sciences, vol. 25, No. 7, pp. 343-346, 2004.

Wasylyk, Christine et al., "p53 mediated death of cells overexpressing MDM2 by an inhibitor of MDM2 interaction with p53", Oncogene, vol. 18, pp. 1921-1934, 1999.

Cordenonsi, Michelangelo et al., "Integration of TGF-β and Ras/MAPK signaling through p53 phosphorylation", Science Express, Sciencemag.org, DOI: 10.1126/science.1135961, 2007.

Shinohara, Kunio et al., "Apoptosis induction resulting from proteasome inhibition", Biochemical Journal, vol. 317, pp. 385-388, 1996.

Kojima, Kensuke et al., "Mdm2 inhibitor nutlin-3a induces p53-mediated apoptosis by transcription-dependent and transcription-independent mechanisms and may overcome atm-mediated resistance to fludarabine in chronic lymphocytic leukemia", Blood, vol. 108, No. 3, pp. 993-1000, 2006.

Alarcon-Vargas, Dania et al., "p53-Mdm2—the affair that never ends", Carcinogenesis, vol. 23, No. 4, pp. 541-547, 2002.

De Graaf, Petra et al., "HdmX protein stability is regulated by the ubiquitin ligase", The Journal of Biological Chemistry, vol. 278, No. 40, issue of Oct. 3, pp. 38315-38324, 2003.

Moll, Ute M., et al., "The MDM2-p53 interaction", Molecular Cancer Research, vol. 1, pp. 1001-1008, 2003.

Patton, John T., et al., "Levels of HdmX expression dictate the sensitivity of normal and transformed cells to nutlin-3", Cancer Research 2006, vol. 66, No. 6, pp. 3169-3176, 2006.

Rohr, Kerstin B., et al., "X-ray structures of free and leupeptin-complexed human αI-tryptase mutants: indication for an α-->β-tryptase transition", Journal of Molecular Biology, vol. 357, pp. 195-209, 2006.

Moldoveanu, T., et al., "Crystal structures of calpain-E64 and--leupeptin inhibitor complexes reveal mobile loops gating the active site", Journal of Molecular Biology, vol. 343, pp. 1313-1326, 2004.

Vassilev, Lyubomir T. et al., "In vivo activation of the p53 pathway by small-molecule antagonists of MDM2", Science, vol. 303, No. 844, DOI: 10.1126/science.1092472, 2004.

Vassilev, Lyubomir T., et al., "Selective small-molecule inhibitor reveals critical mitotic functions of human CDK1", PNAS, vol. 103, No. 28, pp. 10660-10665, 2006.

* cited by examiner

PNC-27 and PNC-28 Effect on Cancer Cells

| CELL LINE | DOSE & PEPTIDE | CELL TYPE | TIME TO TOTAL CELL DEATH ($1\times10^6$) |
|---|---|---|---|
| BMRPA1.TUC-31) | 30mM PNC-28<br>20mM PNC-27 | Rat Pancreatic Cancer<br>Human oncogenic k-rasval12 | 72 h<br>72 h |
| E-49 | 30mM PNC-28 | Rat Brain Angiosarcoma | 72 h |
| B16 | 60mM PNC-27 | Mouse Melanoma | 24 h |
| HeLa | 30mM PNC-28 | Human 5) Cervical Squamous Cell Cancer | 72 h |
| A549 | 30mM PNC-28 | Human Non-small Cell Lung Cancer | 72 h |
| H12992) | 30mM PNC-28 | Human Non-small Cell Lung Cancer p53 null | 1 h |
| MDA-MB-468 3) | 30mM PNC-27 | Human Breast Cancer p53 mutant | 30 min |
| MDA-MB-157 2) | 30mM PNC-27 | Human Breast Cancer; p53 null | 30 min |
| MDA-MB-453 2) | 30mM PNC-27 | Human Breast Cancer; p53 null | 1 h |
| MCF-7 4) | 30mM PNC-27 | Human Breast Cancer | 48 h |
| SW-1417 2) | 30mM PNC-28 | Human Colon Cancer p53 null | 48 h |
| SAOS2 2) | 30mM PNC-28 | Human Osteosarcoma p53 null | 1 h |
| A2058 | 20mM PNC-27 | Human Melanoma | 24 h |
| MIA-PaCa-2 | 75mM PNC-28<br>60mM PNC-27 | Human Pancreatic Cancer | 72 h<br>48 h |
| OVCA1 | 60 µM PNC27 | Primary Human Ovarian cancer | 2h |

FIG. 4

Normal cells are unaffected by PNC-27 treatment

| Cell lines | Dose & peptide | Cell type | Peptide Incubation time |
|---|---|---|---|
| BMRPA-1 | 30 μM PNC-27 | Normal Rat pancreatic acinar | 3 days |
| MCF-10 | 30 μM PNC-27 | Human breast | 24h |

| Primary Human cells | | | |
|---|---|---|---|
| Ag 13145 | 30 μM PNC-27 | Primary Human Fibroblasts | 48h |
| Keratinocytes | 30 μM PNC-27 | Primary Human Keratinocytes | 24h |
| Hematopoetic stem cells | 30 μM PNC-27 | Umbilical cord Stem cells from 5 donors | 14 days |

FIG. 5

Transmission Electron Microscopy of the plasma membrane fractions of BMRPA1 (left) and BMRPA1.TUC3 (right). (Mag. X 85,000)

A          B

Immunoblot of cell lysates and plasma membranes fractions for MDM-2 (90-95kDa) and p53

PNC-28 treated MIA-PaCa-2 cells (10min); (Mag x 46,200)

Scanning Electron Microscopy Images of Human Pancreatic Cancer
Cells (MiaPaCa-2) untreated Scanning Electron Microscopy Images: Human Pancreatic Cancer Cells (MiaPaCa-2 cells) treated with PNC-27 for 30 sec Schematic of the PrecisionShuttle subcloning procedure. The entry and destination vectors are digested with Sgf I and Mlu I, which rarely cut in mammalian coding sequences. After a ligation reaction, the resulting clones are grown on ampicillin-containing medium to select for successful subcloning of the ORF into the destination vector.

SEQUENCE LISTING

```
<160> NUMBER OF SEQ ID NOS: 10

<210> SEQ ID NO 1
<211> LENGTH: 15
<212> TYPE: PRT
<213> ORGANISM: Artificial Sequence
<220> FEATURE:
<223> OTHER INFORMATION: peptide; amino acid residues 12-26 of human p53
      protein

<400> SEQUENCE: 1

Pro Pro Leu Ser Gln Glu Thr Phe Ser Asp Leu Trp Lys Leu Leu
1               5                   10                  15

<210> SEQ ID NO 2
```

```
<211> LENGTH: 10
<212> TYPE: PRT
<213> ORGANISM: Artificial Sequence
<220> FEATURE:
<223> OTHER INFORMATION: peptide; amino acid residues 17-26 of human p53
      protein

<400> SEQUENCE: 2

Glu Thr Phe Ser Asp Leu Trp Lys Leu Leu
1               5                   10

<210> SEQ ID NO 3
<211> LENGTH: 17
<212> TYPE: PRT
<213> ORGANISM: Artificial Sequence
<220> FEATURE:
<223> OTHER INFORMATION: membrane resident peptide (MRP), Antennapedia

<400> SEQUENCE: 3

Lys Lys Trp Lys Met Arg Arg Asn Gln Phe Trp Val Lys Val Gln Arg
1               5                   10                  15

Gly

<210> SEQ ID NO 4
<211> LENGTH: 13
<212> TYPE: PRT
<213> ORGANISM: Artificial Sequence
<220> FEATURE:
<223> OTHER INFORMATION: Sequence from cytochrom P450, used as a control

<400> SEQUENCE: 4

Met Pro Phe Ser Thr Gly Lys Arg Ile Met Leu Gly Glu
1               5                   10

<210> SEQ ID NO 5
<211> LENGTH: 32
<212> TYPE: PRT
<213> ORGANISM: Artificial Sequence
<220> FEATURE:
<223> OTHER INFORMATION: PNC-27

<400> SEQUENCE: 5

Pro Pro Leu Ser Gln Glu Thr Phe Ser Asp Leu Trp Lys Leu Leu Lys
1               5                   10                  15

Lys Trp Lys Met Arg Arg Asn Gln Phe Trp Val Lys Val Gln Arg Gly
                20                  25                  30

<210> SEQ ID NO 6
<211> LENGTH: 27
<212> TYPE: PRT
<213> ORGANISM: Artificial Sequence
<220> FEATURE:
<223> OTHER INFORMATION: PNC-28

<400> SEQUENCE: 6

Glu Thr Phe Ser Asp Leu Trp Lys Leu Leu Lys Lys Trp Lys Met Arg
1               5                   10                  15

Arg Asn Gln Phe Trp Val Lys Val Gln Arg Gly
                20                  25

<210> SEQ ID NO 7
<211> LENGTH: 30
<212> TYPE: PRT
<213> ORGANISM: Artificial Sequence
<220> FEATURE:
<223> OTHER INFORMATION: PNC-29 (Control Peptide)
```

<400> SEQUENCE: 7

Met Pro Phe Ser Thr Gly Lys Arg Ile Met Leu Gly Glu Lys Lys Trp
1               5                   10                  15

Lys Met Arg Arg Asn Gln Phe Trp Val Lys Val Gln Arg Gly
            20                  25                  30

<210> SEQ ID NO 8
<211> LENGTH: 35
<212> TYPE: PRT
<213> ORGANISM: Artificial Sequence
<220> FEATURE:
<223> OTHER INFORMATION: PNC-27-Leupeptin
<220> FEATURE:
<221> NAME/KEY: misc_feature
<223> OTHER INFORMATION: acetyl moiety, CHO, attached to Arg at 35

<400> SEQUENCE: 8

Pro Pro Leu Ser Gln Glu Thr Phe Ser Asp Leu Trp Lys Leu Leu Lys
1               5                   10                  15

Lys Trp Lys Met Arg Arg Asn Gln Phe Trp Val Lys Val Gln Arg Gly
            20                  25                  30

Leu Leu Arg
        35

<210> SEQ ID NO 9
<211> LENGTH: 30
<212> TYPE: PRT
<213> ORGANISM: Artificial Sequence
<220> FEATURE:
<223> OTHER INFORMATION: PNC-28-Leupeptin
<220> FEATURE:
<221> NAME/KEY: Misc_Feature
<223> OTHER INFORMATION: Acetyl Moiety, CHO, attached to Arg at 30

<400> SEQUENCE: 9

Glu Thr Phe Ser Asp Leu Trp Lys Leu Leu Lys Lys Trp Lys Met Arg
1               5                   10                  15

Arg Asn Gln Phe Trp Val Lys Val Gln Arg Gly Leu Leu Arg
            20                  25                  30

<210> SEQ ID NO 10
<211> LENGTH: 8
<212> TYPE: PRT
<213> ORGANISM: Artificial Sequence
<220> FEATURE:
<223> OTHER INFORMATION: non-native p53
<220> FEATURE:
<221> NAME/KEY: MISC_FEATURE
<223> OTHER INFORMATION: Acetyl moiety, CHO, attached to Phe at
      position 1
<220> FEATURE:
<221> NAME/KEY: MISC_FEATURE
<223> OTHER INFORMATION: NH2 attached to Leu at position 8
<220> FEATURE:
<221> NAME/KEY: MISC_FEATURE
<222> LOCATION: (3)..(3)
<223> OTHER INFORMATION: Xaa in position 3 denotes an alpha-amino-
      isobutyric acid
<220> FEATURE:
<221> NAME/KEY: MISC_FEATURE
<222> LOCATION: (4)..(4)
<223> OTHER INFORMATION: Xaa in position 4 denotes phosphonomethyl-
      phenylalanine
<220> FEATURE:
<221> NAME/KEY: MISC_FEATURE
<222> LOCATION: (5)..(5)
<223> OTHER INFORMATION: Xaa in position 5 denotes 6-chlorotryptophan
<220> FEATURE:

```
<221> NAME/KEY: MISC_FEATURE
<222> LOCATION: (7)..(7)
<223> OTHER INFORMATION: Xaa in position 7 denotes 1-amino-
      cyclopropanecarboxylic acid

<400> SEQUENCE: 10

Phe Met Xaa Xaa Xaa Glu Xaa Leu
1               5
```

SMALL MOLECULE CANCER TREATMENTS THAT CAUSE NECROSIS IN CANCER CELLS BUT DO NOT AFFECT NORMAL CELLS

CROSS REFERENCE TO RELATED APPLICATION

This patent application is the national stage of international application number PCT/US08/84810, filed Nov. 26, 2008, which claims the benefit of and priority to U.S. Provisional Patent Application Ser. No. 60/990,276 filed on Nov. 26, 2007, the contents of each of which are incorporated herein by reference in their entireties.

FUNDING STATEMENT

The present invention was made possible by funding from the American College of Surgeons Faculty Fellowship Research Award and award identifier USPHS NIH CA 42500, and from the Lustgarten Foundation for Pancreatic Cancer Research. The government may have certain rights to the invention.

FIELD OF THE INVENTION

The present invention is directed to an HDM-2-targeting cancer treatment. Specifically, the present invention is directed to methods of various cancer treatments that target HDM-2 in cancer cells, killing cancer cells by necrosis while not affecting normal, non-cancerous cells.

BACKGROUND

New approaches to cancer treatments are needed to yield effective and efficient cancer treatments. Some cancer treatments are directed to the p53 mechanism within cells. The p53 protein blocks the oncogenic effects of a number of oncogenic proteins that induce mitosis. Absence of the p53 protein is associated with cell transformation and malignant disease.

Cancer treatments which target the p53 protein within the cancer cells have been developed recently. However, some types of cancer cells do not have p53, while others exhibit p53 in a mutated, inactive form. Thus, these p53 targeting cancer treatments are ineffective at treating cancers as these treatments do not have any effect on cells with inoperative (mutant) or nonexistent p53. Also, normal non-cancerous cells have p53, so it is unclear what detrimental affects these treatments may have on non-cancerous cells.

SUMMARY OF THE INVENTION

In an aspect of the present invention, a method of treating cancer in a subject is provided. The method includes: providing a subject having a plurality of cancer cells; and administering to the subject, a therapeutically effective amount of a composition including: an HDM-2 binding component; and a membrane resident component (or membrane resident peptide, 'MRP'), the membrane resident component bound to the HDM-2 binding component.

In another aspect of the present invention, a method of selectively necrosing cells is provided. The method includes: providing a plurality of cells, including at least one cancer cell and at least one normal non-cancerous cell; administering to the cells a composition, where the composition includes an HDM-2 binding component and a membrane resident component, the membrane resident component bound to the HDM-2 binding component; where the composition results in membranolysis of one or more of the cancer cells, but does not affect the normal non-cancerous cells.

In still another aspect of the present invention, a method of causing membranolysis in cancer cells is provided. The method includes: administering to at least one cancer cell a compound including an HDM-2 binding component and a membrane resident component, the membrane resident component bound to the HDM-2 binding component.

In yet another aspect of the present invention, a cancer treatment composition is provided. The composition includes: an HDM-2 binding component; and a membrane resident component, where the membrane resident component is attached to the HDM-2 binding component, where the composition causes selective membranolysis when administered to a sample of cells, the sample containing a plurality of cancer cells and a plurality of normal non-cancerous cells, further where membranolysis only occurs in the cancer cells.

The embodiments of the present invention may be better understood through a study of the following drawings and detailed description.

BRIEF DESCRIPTION OF THE DRAWINGS

FIG. 4 is a table outlining various cancer cell lines to which PNC-27 or PNC-28 were administered, further depicting the time to total cell death.

FIG. 5 is a table depicting that various untransformed cell lines and primary human cells were unaffected when incubated with PNC-27 for one to several days.

DETAILED DESCRIPTION

Figure 1:
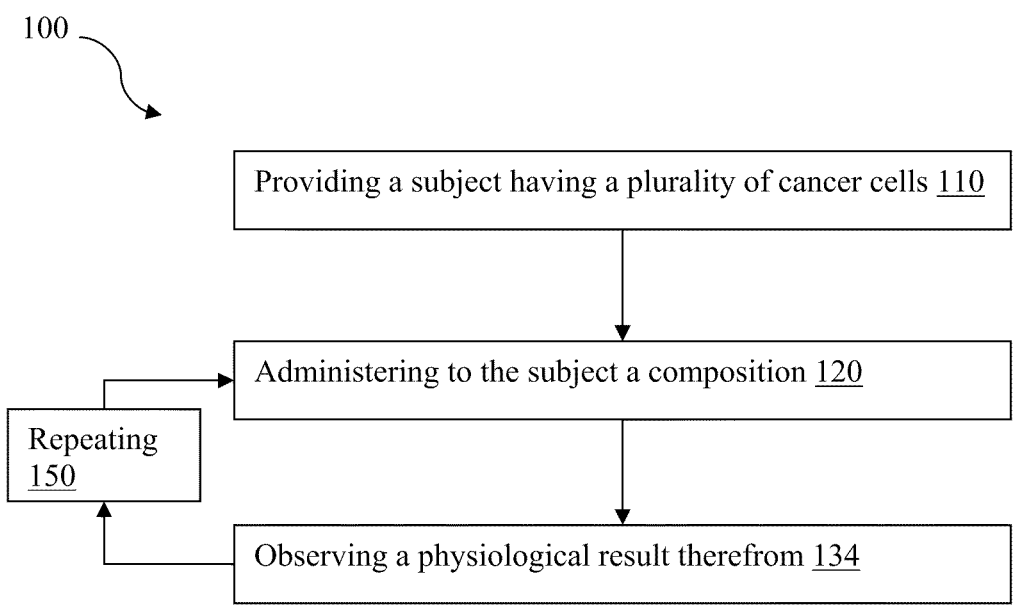
FIG. 1 depicts a method of treating cancer in a subject.

This invention relates to the surprising discovery by the present inventors of the selective mechanism of action of certain peptides; that when administered to cancer cells and normal non-cancerous cells, necrosis of cancer cells occurs, but the normal non-cancerous cells are unaffected. This surprising result led to the invention of the novel methods to treat cancer, and compositions of the present invention for treating the same. More specifically, this invention involves methods of treatment and compositions of synthetic peptide, non-peptide, and combination molecules for treating cancer, where the compounds selectively destroy malignant and transformed cells only, even when administered to a mixture of normal non-cancerous cells and cancer cells. Also included are methods of treating cancer.

As is known, the p53 protein is a vital regulator of the cell cycle. It blocks the oncogenic effects of a number of oncogene proteins that induce mitosis, in part by blocking transcription of proteins that induce mitosis and by inducing the transcription of proteins that block mitosis, and promotes apoptosis. Absence of the p53 protein is associated with cell transformation and malignant disease. Haffner, R & Oren, M. (1995) Curr. Opin. Genet. Dev. 5: 84-90.

The p53 protein molecule consists of 393 amino acids. It includes domains that bind to specific sequences of DNA in a DNA-binding domain that consists of residues 93-312. The crystal structure of this region has been determined by x-ray crystallography. Residues 312-393 are involved in the formation of homotetramers of the p53 protein. Residues 1-93 constitute the trans-activating domain and are involved in regulation of the activity and half life of the p53 protein.

The gene encoding the p53 protein is that is gene most commonly disrupted in cancer. p53 protein acts as the guardian of the genome, as it guards against copying of DNA. It was previously established that the p53 gene within cells was a target treatment for cancer. However, p53 targeting treatment in cancer cells has various problems associated with it that limits the use of p53 targeting treatments. For example, not all cancers exhibit p53 in the cell. Targeting treatments for these types of cancers would not work, as there is no p53 for the targeting compounds to bind to. Also, some cancers exhibit a mutated form of p53, which is inactive. As mutant p53 is inactive in these cancers, targeting compounds also do not work for these cancers. Thus, p53 dependent treatment mechanisms are ineffective against these types of cancer.

The p53 protein binds to another important regulatory protein, the HDM-2 protein. As used herein, "MDM-2" refers to the regulatory protein in mice, "RDM-2" refers to the regulatory protein in rats, while "HDM-2" refers to the regulatory protein in humans. MDM-2 and HDM-2 have substantially similar roles in cancer cells, so experiments related to the function and role of the protein may be completed with either human cells (studying HDM-2), rat cells (studying RDM-2), or mouse cells (MDM-2). The HDM-gene that encodes the HDM-2 protein is a known oncogene. The HDM-2 protein forms a complex with the p53 protein, which results in the degradation of the p53 protein by a ubiquitination pathway. The p53 protein binds to HDM-2 protein using an amino acid (AA) sequence that includes residues 12-26 of the p53 protein, which are invariant. The entire HDM-2 protein binding domain of the p53 protein spans residues 12-26. Haffner, R & Oren, M. (1995) Curr. Opin. Genet. Dev. 5: 84-90. The HDM-2 protein is the expression product of a known oncogene, so the HDM-2 protein is a very important regulatory protein.

Some cancer treatments have been developed that utilize molecules to block the formation of the complex between the p53 protein and the MDM-2 protein that causes the inhibition of transcriptional activity of the p53 protein. Thus the anti-tumor effect of these molecules prolong the half-life of wild-type p53 enhancing its anti-tumor activity. More generally, these and other experimental observations have been interpreted as suggesting that the anti-tumor effect of the p53 protein might be enhanced by peptides capable of interfering with the binding of the MDM-2 protein to the p53 protein which is thought to result in an extension of the life-span (t/2) of p53 and in an increase in the cellular level of p53. Indeed, a number of investigators have suggested that the MDM-2/p53 complex might be a target for rational drug design. See, e.g., Christine Wasylyk et al., "p53 Mediated Death of Cells Overexpressing MDM-2 by an Inhibitor of MDM-2 Interaction with p53", Oncogene, 18, 1921-34 (1999), and U.S. Pat. No. 5,770,377 to Picksley et al.

The inventors of the present invention have surprisingly discovered that cancer cells have roughly five times as much HDM-2 in their cell membranes as do normal non-cancerous cells. This novel discovery has led the present inventors to design new compositions and methods of treating cancer that focus on and take advantage of the newly discovered knowledge related to HDM-2.

As used herein, cancer includes any disease or disorder associated with uncontrolled cellular proliferation, survival, growth, or motility. Cancers that may be treated or prevented by the present invention include any cancer whose cells have increased expression of HDM-2 in their plasma membranes. Such cancers may include, for example, pancreatic cancer, breast cancer, colon cancer, gastric cancer, prostate cancer, thyroid cancer, ovarian cancer, endometrial cancer, glioblastoma, astrocytoma, renal carcinoma, lung cancer, sarcoma, including osteogenic sarcoma, mesothelioma, sporadic non-familial tumors, lymphoma, and others including hematologic cancers such chronic myelogenous leukemia. Precancerous conditions, where cells exhibit high amounts of HDM-2 in the plasma membrane, are also included as treatable with the compositions and methods of the present invention.

Specifically, the inventors have designed novel non-p53 cancer treatments that focus on the characteristics of cancer cells in a targeted cancer cell treatment. One aspect of the composition includes a membrane transport component, which is quickly and effectively transported through the cancer cell membrane. The other aspect of the composition includes an HDM-2 binding component, which targets HDM-2 in the cell membrane, and binds to the HDM-2 therein. The two components are attached, (e.g., chemically bound to each other), so that, while the membrane resident component (e.g. the membrane resident peptide (or MRP)) inserts into the cancer cell membrane, the HDM-2 binding component attaches to the HDM-2 in the cancer cell membrane. This interaction between the HDM-2-binding segment and HDM-2 in the membrane holds the peptide in the membrane in which it adopts a membrane-active conformation allowing it to form pores in the cancer cell membrane.

This results in rapid tumor cell necrosis. A similar phenomenon occurs at the mitochondrial membrane within the cancer cell where significant amounts of HDM-2 are also present.

Thus, the administration of the compositions to one or more cancer cells results in the formation of pores in the cell membranes of the cancer cells. The presence of the membrane resident peptide on the end of the HDM-2 binding component allows the peptide to become membrane-active and to form well-defined pores in the cell membrane, causing membranolysis, which allow for extrusion of the intracellular contents from the interior of the cancer cell, resulting in the compromise of the integrity of the cell. Pores in the cancer cell membrane are formed as an immediate result of administration of the compound. After the pores are formed, cell necrosis, or cell death, results within a short time frame, ranging from 15 minutes to 48 hours. Pore formation in the plasma membrane, in turn, causes membranolysis of the cancer cells, as the holes in the cell walls start allowing excess fluid and free compound to rush into the cells which, simultaneously, start leaking cytoplasm into the surrounding environment. The compound entering the cells through the plasma membrane pores binds to the HDM-2 and forming pores in the mitochondrial membrane causing lysis of the mitochondria and the abrupt termination of cellular energy production. Once membranolysis starts, the cell eventually undergoes necrosis, or cell death, as a result of the treatment with the methods and compositions of the present invention.

Therefore, the compositions and methods of treatment have devastating effects on cancer cells. Normal, non-cancerous cells are unaffected, as normal cells have from none to negligible amounts of HDM-2 in their plasma membranes as compared to cancer cell membranes. Even if the composition is transported into normal cells (as through membrane transport of the membrane resident component), the composition has no measurable effect on the normal, non-cancerous cells.

Thus, not only do the methods and compositions of the present invention tend to eradicate cancer cells, they may be administered to cancer cells and healthy cells alike, and only cancer cells will be affected. Further, as the proposed mechanism of action is non-p53 targeting, these methods and compounds will be effective in the treatment of more varieties of cancer, including those cancers which have no p53 present, or an inactive p53 as the result of mutation. Additionally, these treatments may be effective against cancers which, due to their location in the body, may otherwise be considered undetectable or inoperable. Thus, the methods and compositions of the present invention solve the problems associated with p53 targeting treatments and provide an effective and efficient treatment of cancer cells in a subject, preferably a mammal, more preferably a human.

The materials and methods of the present invention provide novel methods of treatment that are directed to the newly discovered common characteristic of various forms of cancer, the presence of HDM-2 in the cancer cell membrane. Such materials and compositions may be used as a general treatment to many forms of cancer, which, up until now, may have very different treatment options and/or varying degrees of success.

Though cancers may not exhibit similar characteristics pathologically or physiologically within subjects diagnosed therewith, or typical treatment avenues, many of these cancers, though admittedly different, have high levels of HDM-2 present in their cell membranes. Cancers that have been identified as having a large amount of HDM-2 in the cell membrane include, for example: MIA-PaCa-2 human pancreatic cancer cells, BMRPA1.TUC-3 rat pancreatic cancer cells, MCF-7 human breast cancer cells, B16 mouse melanoma, and a human melanoma A2025 cells.

The compositions of the present invention have both an HDM-2 binding domain and a membrane resident component (or membrane resident peptide), thus, the compositions have selectivity and a high affinity for cancer cells, and will thus only bind to and cause necrosis of cancer cells when administered to a combination of cancer cells and normal, healthy cells. These new methods and compositions provide effective treatments, screening methods for additional novel drug candidates, and other benefits and advantages over the current state of the art.

The compositions of the present invention which are employable with the methods of the present invention include generally an HDM-2 binding site and a membrane resident component, or membrane resident peptide. Molecules that bind to HDM-2 may be composed of residues that are shared by the p53 HDM-2 binding domain, or may alternatively, be small molecules with a tendency or high affinity for binding to HDM-2.

Thus, these methods may be used to treat a sample of cells containing both non-cancerous, normal cells and cancer cells. Such samples would include cell lines, tissue samples, tumors, and/or a subject having cancer in need of treatment. As the methods of treatment do not cause cell death of normal cells, these methods of treatment are focused on the cancer cells, irrespective of the mode of administration to the cell sample. Thus, these methods of treatment may be used for tumors or cancers that are widespread, inoperable, or otherwise not effectively treated with conventional means or combination therapies.

The present invention provides methods of using peptides which correspond to all or a portion of amino acid residues 12-26 of human p53 protein. When fused to a membrane resident peptide (or non-peptide, membrane resident component) the peptides are lethal to malignant or transformed cells. The subject peptides are thus useful in treating cancer in an animal, preferably a human.

The compositions of the present invention may include, for example, PNC-27 and PNC-28, as disclosed and described in pending U.S. patent application Ser. No. 11/977,521, filed on Oct. 25, 2007 (U.S. Publication No. 20080076713), and Ser. No. 11/582,687, filed on Oct. 26, 2006 (U.S. Publication No. 20070238666), the contents of both of these applications are incorporated by reference herein in their entireties.

Additionally, one or more compositions may be used, where a compound may have both shared residues of p53 as an HDM-2 binding domain, and also membrane resident component. The inventors of the present invention have developed a peptide from the HDM-2-binding domain of p53 attached to a membrane resident peptide (or component) sequence that causes necrosis, not apoptosis, of tumor, but not normal, non-cancerous cells. The peptides include both PNC-27 and PNC-28, which are p53-derived peptides from the human double minute binding domain (HDM-2) that are attached to the membrane resident peptide (MRP). These synthetic peptides induce cell necrosis of cancer cells, but not normal non-cancerous cells. The anti-cancer activity and mechanism of PNC-27 (p53 aa12-26-MRP) and PNC-28 (p53 AA 17-26-MRP) were specifically studied by the inventors of the present invention as against human pancreatic cancer, though uses and applications are included with the various methods of the present invention.

Preferably, the membrane resident peptide, which, besides being necessary for cell membrane insertion, stabilize includes predominantly positively charged amino acid residues since a positively charged sequence, as it stabilizes the alpha helix of a subject peptide or small molecule component. Examples of MRPs that may be employed are referenced in U.S. patent application Ser. No. 11/997,521 filed on Oct. 25, 2007, published as United States Patent Application Publication No. 20080076713, the contents of which are incorporated herein by reference in its entirety. Additional examples of MRP sequences which may be linked to the HDM-2 binding peptides of the present invention are described in Futaki, S. et al (2001) Arginine-Rich Peptides, J. Biol. Chem. 276, 5836-5840.

It should be noted that p53 targeting cancer treatments and HDM-2 targeting cancer treatments cause cell death through different modes. As is known, cell death can occur through either necrosis or apoptosis. p53-targeting treatments typically cause cell death through apoptosis, while the embodiment features of the present invention cause cell death by necrosis. Necrosis is uncontrolled cell death, while apoptosis is genetically controlled or "programmed" cell death. Apoptosis is the deliberate cellular response to specific environmental and developmental stimuli or programmed cell death. Cells undergoing apoptosis exhibit cell shrinkage, membrane blebbing, chromatin condensation and fragmentation. In contrast, necrosis involves the destruction of cytoplasmic organelles and a loss of plasma membrane integrity. Apoptosis of cancer cells by p53 targeting treatments fails to treat those cancers that do not exhibit p53, or, through mutations, exhibit an inactive p53 form that is unresponsive to p53 targeted treatments.

Referring to FIG. 1, a method 100 of treating cancer in a subject is provided. The method 100 includes: providing 110 a subject having a plurality of cancer cells; and administering 120 to the subject, a therapeutically effective amount of a composition including: an HDM-2 binding component; and a membrane resident component, the membrane resident component bound to the HDM-2 binding component. The method may further comprise the step of observing a physiological result 134. As referenced herein, observing a physiological result may refer to observing a change to one or more cancer cells and/or observing a change in a living subject. Changes may be observed through changes in cell characteristics, including pore formation on the plasma membrane of cancer cells. Further, observations may be made, for example, for extrusion from the treated cancer cell of an increased amount of lactate dehydrogenase (LDH), a cytosolic enzyme, in the cellular medium and/or the observation of necrosis in cells. One or more assays and/or experiments may be completed in order to observe a result of the method 100 of the present invention.

Figure 2:
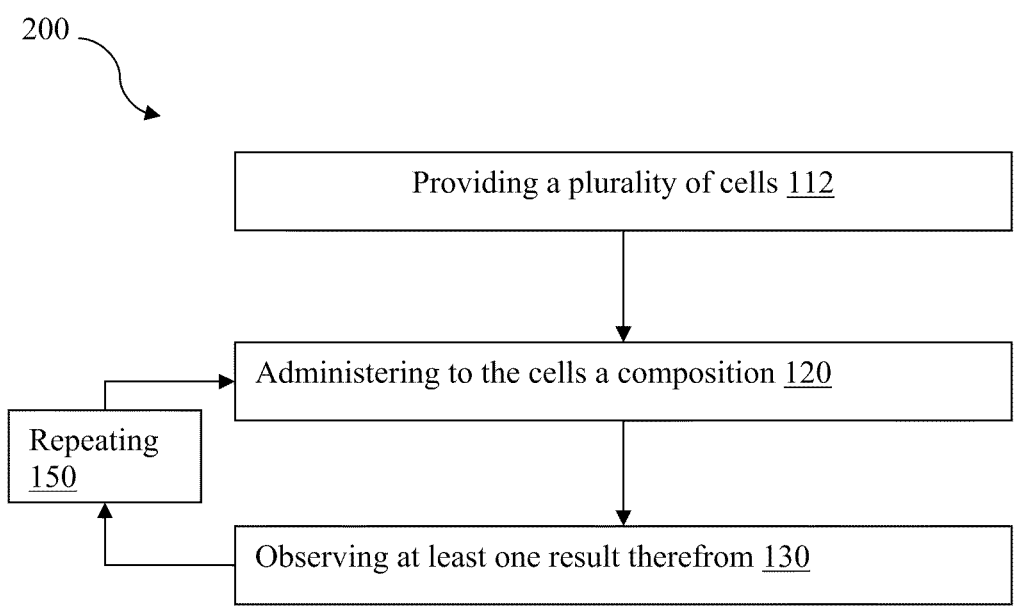
FIG. 2 depicts a method of selectively necrosing cells.

Referring to FIG. 2, a method 200 of selectively necrosing cells is provided. The method includes: providing 112 a plurality of cells, including at least one cancer cell and at least one normal non-cancerous cell; administering 120 to the cells a composition, wherein the composition includes an HDM-2 binding component and a membrane resident component, the membrane resident component bound to the HDM-2 binding component; wherein the composition results in membranolysis of the cancer cells, but does not affect the normal non-cancerous cells. The step of providing 112 a plurality of cells may be, for example, providing at least one cell line, providing a cell sample, tissue sample, tumor sample, or a live subject having cancer. The method 200 refers to "selectively necrosis" as only the cancer cells from a mixture of cancer cells and healthy cells, will be killed, or necrotized.

Figure 3:
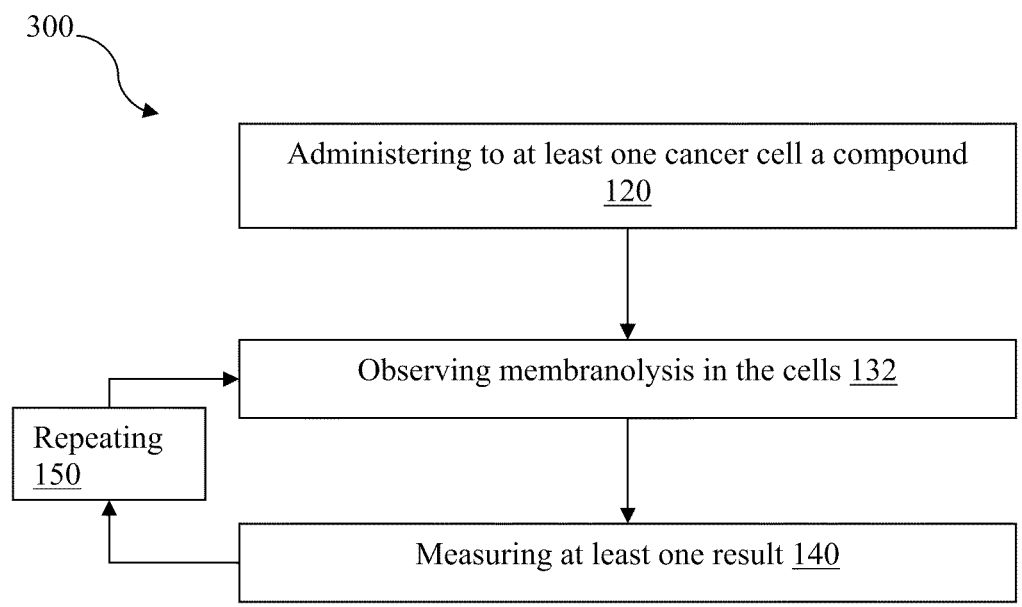
FIG. 3 depicts a method of causing membranolysis in cancer cells.

Referring to FIG. 3, a method 300 of causing membranolysis in cancer cells is depicted. The method includes: administering 120 to at least one cancer cell a compound including an HDM-2 binding component and a membrane resident component, the membrane resident component bound to the HDM-2 binding component. The method 300 may further include the step of observing at least one result thereof 132, such as membranolysis. Observable results may include observing the results of the administration 120 step, as through visual inspection, or microscopic inspection.

Further, the method 300, as well as the methods 100 and 200, may include the step of measuring at least one result 140. Measuring 140, as used herein, indicates that more than mere passive observation is completed. Measuring 140 may encompass administering various assays and analytical tests to ascertain or analyze one or more results of the administration step. Such analytical tests and assays are described herein.

It should also be noted that one or more of the steps of the methods 100, 200, 300, as set forth herein, may be repeated or reiterated 150 until a desired result is reached. A desired result may be a certain percentage of necrosis in the cancer cells, a reduced tumor size in a subject, and the like. Repeated a reiterated 150 administration may, for example, include a treatment regimen or therapy designed by a clinician or a doctor.

The step of providing 110 as set forth within methods 100, 200 and 300, may include, for example, providing a living subject diagnosed with cancer, suspected of having cancer, refractory, or relapse, or a subject who has been transplanted or xenotransplanted with cancerous cells. The plurality of cells, as referenced herein, may refer to a cell, a cell line, a plurality of cells in vivo, a combination of two or more types of cells (i.e. cancerous and non-cancerous cells), a tumor, more than one tumor, and the like.

A composition with "activity" as a cancer treatment with reference to the embodiments of the present invention refers to an ability to induce a desirable effect upon in vitro, ex vivo, or in vivo administration of the compound. Desirable effects include preventing or reducing the likelihood (increasing the likelihood or causing) one or more of the following events: binding to HDM-2 in cancer cells, insertion into the cancer cells' plasma membrane, assembly and pore foundation, transport across the cancer cell membrane, causing membranolysis.

The terms "therapeutically effective dosage" and "effective amount" refer to an amount sufficient to kill one or more cancer cells. A therapeutic response may be any response that a user (e.g. a clinician will recognize) exhibits as an effective response to the therapy, including the foregoing symptoms and surrogate clinical markers. Thus, a therapeutic response will generally be an amelioration or inhibition of one or more symptoms of a disease or disorder, e.g. cancer.

The term subject, as used herein may refer to a patient or patient population diagnosed with, or at risk of developing one or more forms of cancer. Also, as used herein, a subject may refer to a living animal, including mammals, which may be given cancer through transplantation or xenotransplanting which may be subsequently treated with the methods and compounds of the present invention or which have developed cancer and need veterinary treatment. Such subjects may include mammals, for example, laboratory animals, such as mice, rats, and other rodents; monkeys, baboons, and other primates, etc. They may also include household pets or other animals in need of treatments for cancer.

Further to the methods 100, 200, and/or 300, the administration step 120 may be done through various forms, as is known. Administration of the synthetic peptides of the present invention may be by oral, intravenous, intra-arterial, intranasal, suppository, intraperitoneal, intramuscular, intradermal or subcutaneous administration or by infusion or implantation. When administered in such manner, the synthetic peptides of the present invention may be combined with other ingredients, such as carriers and/or adjuvants. There are no limitations on the nature of the other ingredients, except that they are preferably pharmaceutically acceptable, efficacious for their intended administration, preferably do not degrade the activity of the active ingredients of the compositions, and preferably do not impede importation of a subject peptide into a cell. The compounds may also be impregnated into transdermal patches, or contained in subcutaneous inserts, preferably in a liquid or semi-liquid form which patch or insert time-releases therapeutically effective amounts of one or more of the subject synthetic compounds.

The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents.

Administering may include contacting. The term "contacting" refers to directly or indirectly bringing the cell and the compound together in physical proximity. The contacting may be performed in vitro or in vivo. For example, the cell may be contacted with the compound by delivering the compound into the cell through known techniques, such as microinjection into the tumor directly, injecting the compound into the bloodstream of a mammal, and incubating the cell in a medium that includes the compound.

The compounds of the invention are administered to a human in an amount effective in achieving its purpose. The effective amount of the compound to be administered can be readily determined by those skilled in the art, for example, during pre-clinical trials and clinical trials, by methods familiar to physicians and clinicians. Typical daily doses include approximately 1 mg to 1000 mg.

Any method known to those in the art for contacting a cell, organ or tissue with a compound may be employed. Suitable methods include in vitro, ex vivo, or in vivo methods. In vitro methods typically include cultured samples. For example, a cell can be placed in a reservoir (e.g., tissue culture dish), and incubated with a compound under appropriate conditions suitable for inducing necrosis in cancer cells. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are normally returned to the donor, placed in a recipient, or stored for future use. Thus, the compound is generally in a pharmaceutically acceptable carrier.

In vivo methods are typically limited to the administration of a compound, such as those described above, to a mammal, preferably a human. The compounds useful in the methods of the present invention are administered to a mammal in an amount effective in necrosing cancer cells for treating cancer in a mammal. The effective amount is determined during pre-clinical trials and clinical trials by methods familiar to physicians and clinicians.

An effective amount of a compound useful in the methods of the present invention, preferably in a pharmaceutical composition, may be administered to a mammal in need thereof by any of a number of well-known methods for administering pharmaceutical compounds. The compound may be administered systemically or locally.

The compounds useful in the methods of the invention may also be administered to mammals by sustained release, as is known in the art. Sustained release administration is a method of drug delivery to achieve a certain level of the drug over a particular period of time. The level typically is measured by serum or plasma concentration.

Any formulation known in the art of pharmacy is suitable for administration of the compounds useful in the methods of the present invention. For oral administration, liquid or solid formulations may be used. Some examples of formulations include tablets, capsules, such as gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

Formulations of the compounds useful in the methods of the present inventions may utilize conventional diluents, carriers, or excipients etc., such as those known in the art to deliver the compounds. For example, the formulations may comprise one or more of the following: a stabilizer, a surfactant, preferably a nonionic surfactant, and optionally a salt and/or a buffering agent. The compound may be delivered in the form of an aqueous solution, or in a lyophilized form. Similarly, salts or buffering agents may be used with the compound.

Formulations and Administrations

The compounds of the present invention may be administered in therapeutically effective concentrations, to be provided to a subject in standard formulations, and may include any pharmaceutically acceptable additives, such as excipients, lubricants, diluents, flavorants, colorants, buffers, and disintegrants. Standard formulations are well known in the art. See, e.g. Remington's pharmaceutical Sciences, $20^{th}$ edition, Mach Publishing Company, 2000. The formulation may be produced in useful dosage units for administration by any route that will permit the compound to contact the cancer cell membranes. Exemplary routes of administration include oral, parenteral, transmucosal, intranasal, insulfation, or transdermal routes. Parenteral routes include intravenous, intra-arterial, intramuscular, intradermal, subcutaneous, intraperitoneal, intraductal, intraventricular, intrathecal, and intracranial administrations.

The compounds of the present invention may be administered as a solid or liquid oral dosage form, e.g. tablet, capsule, or liquid preparation. The compounds may also be administered by injection, as a bolus injection or as a continuous infusion. The compounds may also be administered as a depot preparation, as by implantation or by intramuscular injection.

It should also be noted that necrosis of cells generally triggers an immunologic response in the body of a subject, often resulting in inflammation and/or swelling. As such, the methods of the present invention 100, 200, and 300, may also include the step of administering an anti-inflammatory agent or medicament. Many commonly accepted anti-inflammatory agents may be used, as is known in the art.

Yet another embodiment of the present invention provides a cancer treatment composition. The composition includes: an HDM-2 binding component; and a membrane resident component, wherein the membrane resident component is attached to the HDM-2 binding component, wherein the composition causes selective membranolysis when administered to a sample of cells, the sample containing a plurality of cancer cells and a plurality of normal non-cancerous cells, further wherein membranolysis occurs only in the cancer cells.

The compounds and methods 100, 200, 300 of the present invention may be admixed or otherwise combined with a pharmaceutically acceptable carrier. As used herein, a "pharmaceutically acceptable carrier" includes any and all solvents, dispersion media, coatings, antibacterial and antifungal agents, isotonic agents and the like. The use of such media and agents are well-known in the art.

The phase 'pharmaceutically acceptable' refers to molecular entities and compositions that are physiologically tolerable and do not typically produce unwanted reactions when administered to a subject, particularly humans. Preferably, as used herein, the term "pharmaceutically acceptable" means approved by a regulatory agency of the federal or a state government or listed in the U.S. Pharmacopeia or other generally recognized pharmacopeia for use in animals, and more particularly, in humans. The term carrier refers to a diluent, adjuvant, excipient or vehicle with which the compounds may be administered to facilitate delivery. Such pharmaceutical carriers can be sterile liquids, such as water and oils, or organic compounds. Water or aqueous solution saline solutions, and aqueous dextrose and glycerol solutions are preferably employed as carriers, particularly as injectable solutions.

The synthetic peptides of the present invention may be synthesized by a number of known techniques. For example, the peptides may be prepared using the solid-phase technique initially described by Merrifield (1963) in J. Am. Chem. Soc. 85:2149-2154. Other peptide synthesis techniques may be found in M. Bodanszky et al. Peptide Synthesis, John Wiley and Sons, 2d Ed., (1976) and other references readily available to those skilled in the art. A summary of polypeptide synthesis techniques may be found in J. Stuart and J. S. Young, Solid Phase Peptide Synthesis, Pierce Chemical Company, Rockford, Ill., (1984). Peptides may also be synthesized by solid phase or solution methods as described in The Proteins, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, Protective Groups in Organic Chemistry, Plenum Press, New York, N.Y. (1973). The peptides of the present invention may also be prepared by chemical or enzymatic cleavage from larger portions of the p53 protein or from the full length p53 protein. Likewise, membrane-resident sequences for use in the synthetic peptides of the present invention may be prepared by chemical or enzymatic cleavage from larger portions or the full length proteins from which such leader sequences are derived.

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide selectively lethal to malignant and transformed mammalian cells. The present invention also contemplates a deoxyribonucleic acid (DNA) molecule that defines a gene coding for, i.e., capable of expressing a subject peptide or a chimeric peptide from which a peptide of the present invention may be enzymatically or chemically cleaved.

When applied to cells grown in culture, synthetic peptides are selectively lethal to malignant or transformed cells, resulting in a dose-dependent reduction in the cell number. The effect is observable generally within two to three and at most 48 hours.

One or more of the methods 100, 200, 300 may further include the step of determining whether a compound reduces cancer cells activity further includes measuring the level of lactate dehydrongenase (LDH) in the cell medium, observing the cells for pore formation or membranolysis, or observing the cells breaking down over a period of time. The level of necrosis may be measured by any method known in the art, including for example, PCR analysis, RT-PCR, Northern blot, Western blot, immunohistochemistry, ELISA assays, luciferase reporter assays, etc.

One or more of the methods of the present invention may be repeated or reiterated 150 on a subject. This may be desirable, for example, if a subject suffers from refractory or relapse cancer. Also, repeated administration may be desirable if lower dosages are administered repeatedly, over a treatment cycle or pursuant to combination therapy.

Identifying drug candidates typically involves multiple phases. During the early stages, compounds, preferably large libraries of compounds are screened or tested in vitro for binding to and/or biological activity at the cancer cell membrane (with HDM-2 and/or a membrane resident component characteristic). The compounds that exhibit activity ("active compounds" or "hits") from this initial screening process are then tested through a series of other in vitro and in vivo tests to further characterize the anti-cancer normal, non-cancerous tissue and organ protective activity of the compounds.

The in vivo tests at this phase may include tests in non-human mammals such as those mentioned above. If a compound meets the standards for continued development as a drug following in vitro and in vivo tests, the compound is typically selected for testing in humans.

A progressively smaller number of test compounds at each stage are selected for testing in the next stage. The series of tests eventually leads to one or a few drug candidates being selected to proceed to testing in human clinical trials. The human clinical trials may include studies in a human suffering from a medical condition that can be treated or prevented by reducing cancer cells (inducing cancer cell necrosis).

The compounds and methods 100, 200, 300 of the present invention may be designed to have one or more desirable characteristics. The desirable characteristics may result in an increased effectiveness when the composition is administered to at least one cancer cell or in vivo to an organism, particularly a mammal, in need of cancer treatment.

Desirably, compounds and compositions of the present invention may have a three dimensional shape or conformation in an alpha-helix-loop-alpha-helix. This is the three-dimensional shape that has been determined by the present inventors for the PNC-27 and PNC-28 peptide-based compositions. The alpha-helix-loop-helix conformation allows the composition to advantageously interact with the cancer cell membrane.

It may also be desirable for the compositions of the present invention to be of a higher degree of rigidity than the synthetic peptides PNC-27 and PNC-28. As is known, peptide-based compositions have natural movement associated with their molecules. As discussed, the alpha-helix-loop-alpha-helix, that results in an amphipathic structure, in which hydrophobic amino acid residues occupy one face of the molecule while polar residues occupy the opposite face of the molecule, is a desired conformation of the molecule. A number of membrane-active peptides, such as melittin and magainin, have these required structures that result in cell membrane lysis though not with the same specificity as PNC-27. Thus, if agents can be administered to a peptide-based composition to increase the rigidity, or if a non-peptide, called a peptidomimetic, rigid molecules of similar size, with a similar amphipathic structure, may be employed with the present invention, then the conformation will more immediately affect the cancer cells. Rosal R, Brandt-Rauf P W, Pincus M R, Wang H, Mao Y, Fine R L. The role of alpha-helical structure in p53 peptides as a determinant for their mechanism of cell death: necrosis versus apoptosis. Adv Drug Deliv Rev 2005; 57:653-60; Pincus, M. R. (2001) "The Physiological Structure and Function of Proteins" in Principles of Cell Physiology (Chapter 2), Third Edition, Ed., N. Sperelakis, Academic Press, New York, pp. 19-42; 3. Dathe, M. and Wieprecht, T. (1999) Structural Features of Helical Anti-Microbial Peptides: Their Potential to Modulate Activity on Model Membranes and Biological Cells. Biochem. Biochem. Biophys. Acta 1462, 71-87.

Another desirable characteristic is for a relatively small-sized composition to be employed with the methods and as the compositions of the present invention. Large peptide, non-peptide, and combination peptide/non-peptide compositions have the disadvantage of triggering an immunogelogic response with a greater likelihood than small molecules, which may go unnoticed in vivo. Thus, the immune system of the organism being treated is less likely to trigger an immune response against small molecules, i.e. peptides of <35AA than large molecule compositions, i.e., proteins with >35AA. Preferably, the synthetic peptide materials of the present invention are on the order of about thirty-five (35) amino acids or fewer.

Generally, as molecules (proteins) exceed 5000 D (~>35AA in size, they become more immunogenic, i.e., they can elicit an immune response in the recipient. Peptides up to 5000 D (<35 AA) have been found to elicit no or only a minor immune response in the recipient. However, long-term (many months) application of peptides from 2500 D to 5000 D can result in stimulating an immune response (they can become immunogenic) in some recipients. Considering the size of our peptides (27AA and 32AA or with Leupeptin 30AA and 35AA) and of the long-life constructs described below, they are all in the non- to borderline-immunogenic range. Taking into account (1) that all PNC-peptides, including those with -leupeptin attached, will have a rather short lifespan (estimates are 10 to 30 min) due to removal by pinocytosis degradation, and (2) that they are applied to tumor-bearing patients most of which are immunologically suppressed, the likelihood of developing immunological responses that will restrict their use is very, very remote.

Yet another desirable characteristic for the composition is to have a long half-life. A composition with a long half-life is able to stay in the body for longer periods of time before decomposing. Thus, a composition with a longer half-life may have an increased longevity, allowing it to be transported through the body to kill more cancer cells or treat cancers located in different parts of the organism upon a single administration. Peptide-based compounds, including PNC-27 and PNC-28, may be altered to include a D-amino acid on the amino terminal end in order to slow peptidase activity of the molecule. Similarly, leupeptin, a known peptidase activity inhibitor, may be attached to the carboxyl terminal end of PNC-27 and PNC-28 in order to slow peptidase activity and lengthen the half-life of the molecules. The synthetic peptides of employed with the methods of the present invention are probably likely to have half-lives on the order of minutes in situ, as is the case for most therapeutic peptides.

To the cancer cell lines depicted in FIG. 4, either PNC-27 or PNC-28 in varying doses were administered to the cancer cells. Cancer cell lines tested include: Rat Pancreatic cancer, Rat Brain Angiosarcoma, Mouse Melanoma, Cervical Squamous Cell Cancer, Non-small cell Lung Cancer (both with p53 and p53 null), Human Breast Cancer (including p53 present, p53 mutant, and p53 null), Human Melanoma, Human Pancreatic Cancer, and Human Ovarian Cancer. To each sample, doses ranging from 60 microMolar to 75 milliMolar were administered to the cancer cells. Total cell death, in cell samples $1 \times 10^6$ cells, occurred in these cell samples as soon as 30 minutes up to about 72 hours. Even with low dosages administered in this experiment, cancer cells were eradicated in a very swift timeframe. This data tends to suggest that lower dosages may be administered to exhibit a therapeutic result. While all doses ultimately kill all of the cancer cells, lower doses tend to take longer to kill the cancer cells than higher doses. For example, at doses of 125 μg/ml and higher, the times vary from 15 minutes to 72 hours, depending on the cancer cell line.

The experimental methods which yielded the data depicted in FIG. 5 are described in sufficient detail for those skilled in the art in the following publications:

Kanovsky, M., Raffo, A., Drew, L., Rosal, R., Do, T., Friedman, F. K., Rubinstein, P., Visser, I., Robinson, R., Brandt-Rauf, P. W., Michl, J., Fine, R. L. and Pincus, M. R. (2001) Peptides from the Amino Terminal mdm-2 Binding Domain of p53, Designed from Conformational Analysis, Are Selectively Cytotoxic to Transformed Cells. Proc. Natl. Acad. Sci. USA 98, 12438-12443;

Do, T. N., Rosal, R. V., Drew, L., Raffo, A. J., Michl, J., Pincus, M. R., Friedman, F. K., Petrylak, D. P., Cassai, N., Szmulewicz, J., Sidhu, G., Fine, R. L. and Brandt-Rauf, P. W. (2003) Preferential Induction of Necrosis in Human Breast Cancer Cells by a p53 Peptide Derived from the mdm-2 Binding Site. Oncogene 22, 1431-1444; and Bowne, W. B., Sookraj, K. A., Vishnevetsky, M., Adler, V., Yadzi, E., Lou, S., Koenke, J., Shteyler, V., Ikram, K., Harding, M., Bluth, M. H., Ng, M., Brandt-Rauf, P. W., Hannan, R., Bradhu. S., Zenilman, M., Michl, J. and Pincus, M. r. (2008) The Penetrating Sequence in the Anti-Cancer PNC-28 Peptide Causes Tumor Necrosis Rather than Apoptosis of Human Pancreatic Cancer Cells. Ann. Surg. Oncol., in press.

Referring to FIG. 5, the table illustrates that the cancer treatment PNC-27, when administered to non-cancerous cells, has no effect. Thirty microMolar dosages were administered to cell types including: normal rat pancreatic acinar cells, human breast cells, primary human fibroblasts, primary human keratinocytes, and umbilical cord stem cells (taken from five donors). The cells were incubated with the PNC-28 or PNC-27 respectively, synthetic peptide for various time frames ranging from one day up to two weeks, with no measurable effect on the non-cancerous cells. This data supports the conclusion of the inventors of the present invention, that the methods and compounds of the present invention have an immediate affect upon cancer cells, causing necrosis in a very short time frame, while having no measurable effect on non-cancerous, healthy cells.

Figure 6:
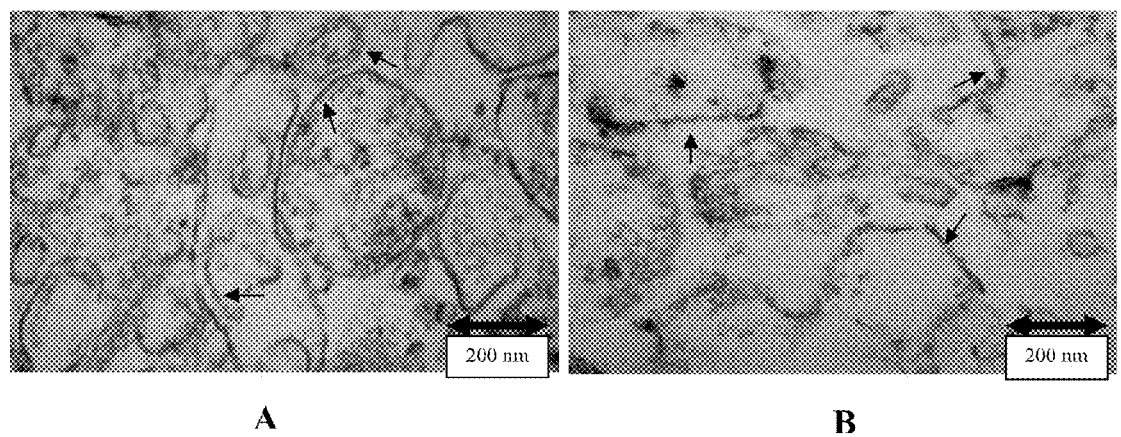
FIG. 6 depicts two transmission electron microscopy (TEM) photographs showing the isolated plasma membrane fractions of BMRPA1 (A, on the left-hand side) and BMRPA1.TUC3 (B, on the right-hand side). Such TEM analyses were performed to monitor plasma membrane purification for the immunoblot (IB) studies summarized in FIG. 7.
Figure 7:
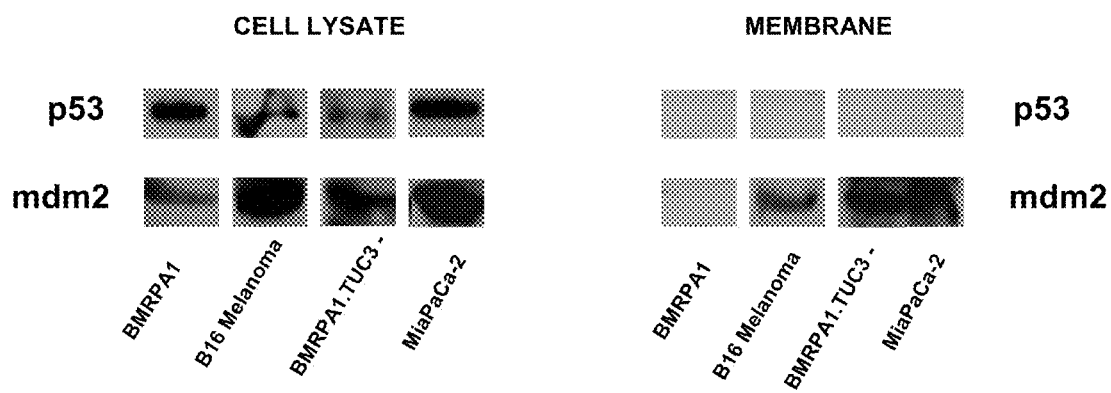
FIG. 7 depicts the IB data of cell lysates and plasma membranes fractions for MDM-2 and p53 of untransformed (rodent primary pancreatic acinar BMRPA1 cells) and cancer cells (mouse B16 Melanoma, rodent pancreatic cancer BMRPA1.TUC3, and human pancreatic cancer MIA PaCA-2 cells).

FIG. 6 depicts the transmission electron microscopy results of the plasma membrane fractions of BMRPA1 (normal rat pancreatic acinar cells) and BMRPA1.TUC3 cells (rat pancreatic cancer-human oncogenic k-ras$^{val12}$). The arrows point to the classic structure of the lipid bilayer of the many plasma membrane sheets and vesicles that have been captured in the two photographs. The photographs demonstrate the significant enrichment of plasma membrane that the purification has achieved. Nevertheless, additional cellular materials are enclosed in the newly formed, mostly inside-out membrane vesicles. Now that we have isolated the plasma membrane fraction of cancer cells and normal cells, we have performed immunoblotting of the plasma membrane proteins and total cell lysates for MDM-2, HDM-2 and p53 as shown in FIG. 7. (Magn. ×85,000).

FIG. 7 shows that MDM-2 and p53 are found, as expected, in the whole cell lysates, while the plasma membrane fractions clearly demonstrate that p53 is not present in the cell membrane of either cancer or normal untransformed cells. In contrast, MDM-2 and HDM-2 are present in the cell membrane of cancer cells, but not in the plasma membrane of untransformed normal cells. Of specific importance in this context is that while whole cell lysates of normal untransformed BMRPA1 cells clearly contain MDM-2 and p53 protein, the cells' plasma membrane are completely devoid of the two proteins. In contrast, the plasma membrane of their BMRPA1.TUC3 daughter cells that had been transformed to cancer cells by direct transfection of oncogenic human k-ras$^{val12}$ contains significant amounts of MDM-2. The absence of p53 in these and the plasma membrane preparations of the other cancer cells further indicates that MDM2 or HDM-2 (human cancer cells) expressed in the cancer cells' plasma membrane is not complexed to p53.

Figure 8:
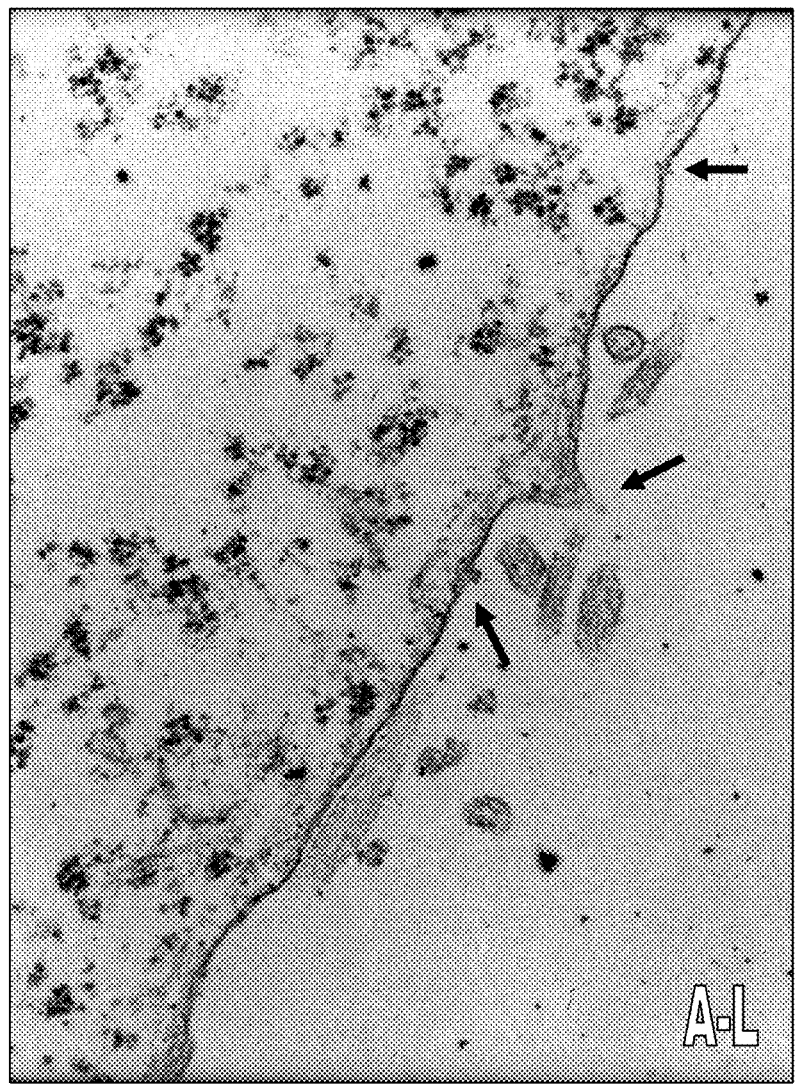
FIG. 8 is a TEM photograph of one human pancreatic cancer cell (MIA-PaCa-2 cell line) taken 10 minutes after PNC-28 administration. The top arrow depicts a pore formed in the cancer cell membrane, the middle arrow depicts an eruption of the cellular membrane in response to the PNC-28, while the bottom arrow depicts a discontinuous region in the cellular membrane as a result of the PNC-28 administration.

FIG. 8 depicts a photograph taken during a Transmission Electron Microscopy study of human pancreatic cancer MIA PaCa-2 cells that had been treated for 10 minutes with PNC-28. The top arrow depicts an area in which a needle-shaped pore has formed in the cancer cell plasma membrane. The middle arrow depicts an area of the cell's plasma membrane that has erupted as a result of PNC-28 acting upon it. The bottom-most arrow depicts an area on the cell's plasma membrane that is discontinuous as a result of PNC-28 administration. From one or more of these areas emphasized with arrows, the cytoplasm will begin to leak from the cell, into the surrounding medium. Extrusion of much of the cells cytoplasmic content through such holes (pores) while the nuclear membrane was still intact was a frequent finding in these and other tumor cells when the incubation period with PNC-28 was extended. Magn. ×42,600.

Figure 9:
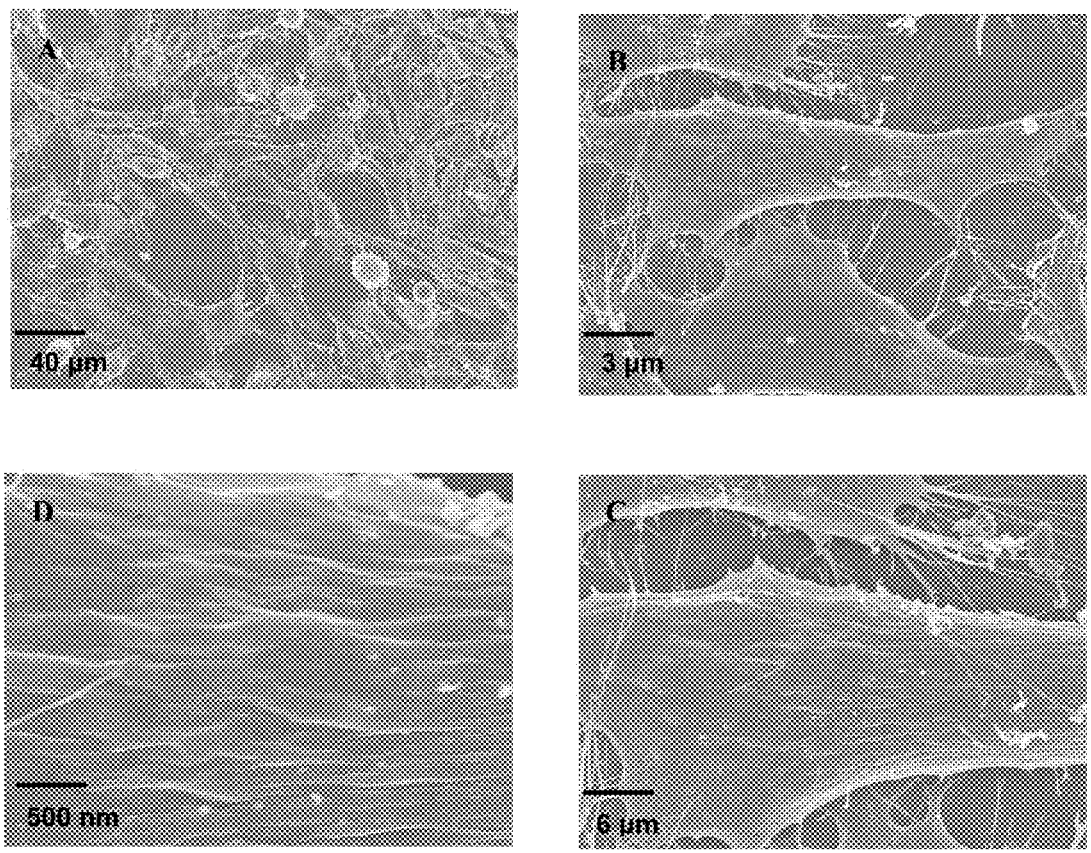
FIG. 9 A-D depict scanning electron microscope (SEM) images of human pancreatic cancer cells that have not been treated with cancer treatments; the cell surfaces are depicted as intact and smooth.
Figure 10:
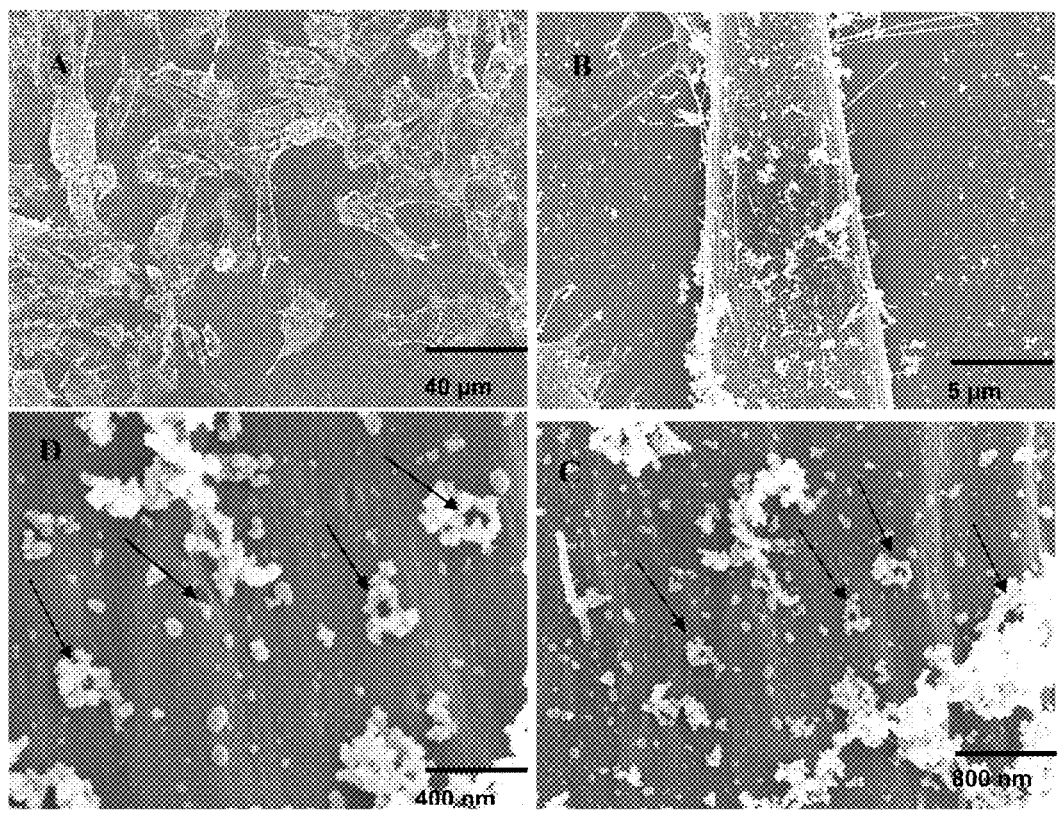
FIG. 10 A-D depict SEM images of human pancreatic cancer cells to which PNC-27 has been administered for 3 min at 37° C.); note the granular surface and pores (arrows) formed on the surface of the cancer cell membranes.

FIGS. 9 and 10 show the before and after PNC-27 treatment images of human pancreatic cancer MIA PaCa-2 cells as observed by scanning electron microscopy (SEM).

In FIG. 9 (A-D), the cell surfaces of the untreated human pancreatic cancer MIA PaCa-2 cells are depicted as relatively continuous and smooth. The appearance of the untreated human pancreatic cancer MIA PaCa-2 cells as shown in FIG. 9 is in stark contrast with the human pancreatic cancer MIA PaCa-2 cell images of FIG. 10, which have been treated with PNC-27 for 3 min at 37° C. Referring to FIGS. 10, A and B, the human pancreatic cancer MIA PaCa-2 cells have a granular appearance on their surfaces. This is the PNC-27 that has gathered on and about the cancer cell membrane, presumably in complex with HDM-2.

As is shown in FIGS. 10, C and D, dark discontinuous regions, or pores, have been formed in the cancer cell membranes. For ease in reference, some of the pores in FIGS. 10 C and D are emphasized with arrows pointing towards the pore. Also, about many of the pores, there are gatherings or clumps of PNC-27. This tends to suggest that not only is PNC-27 forming pores in the cancer cell membranes, but also that PNC-27 that has not become membrane active may enter the cancer cell through the pores formed by other PNC-27 molecules. (Magnifications are evident by the bars.)

Since PNC-27 has an HDM-2 binding domain and since HDM-2 occurs in the membranes of cancer cells but normal cells and since PNC-27 is selectively toxic to cancer cells but not normal cells, we concluded that PNC-27 binds to HDM-2 in the cancer cell membrane. We performed two sets of experiments to prove this conclusion. In the first set of experiments, in the first set of experiments, we performed co-localization studies. To show analytically that PNC-27 co-localizes with HDM-2, in the plasma cell membrane, experiments were performed with fluorescent-labeled antibodies.

Cancer cells were treated with PNC-27 at a dose of 125 ug/ml (its IC$_{50}$) or lower concentrations, like 25 ug/ml, that will allow binding of the peptide to HDM-2 but will not rapidly kill the cells. After the cells were treated, the cells were incubated first with the anti-p53 antibody that recognizes p53 residues 12-26. This antibody is called DO-1, and it is labeled with FITC, a green fluorescent probe. The cells were washed free of any excess antibody. Then the cells were incubated with an anti-HDM-2 antibody that was been conjugated to a red fluorescent dye. After washing the cells free of excess antibody, the cells were subjected to confocal microscopy. We found that the red and green fluorescence occurred together, in the cell membrane only, giving a well-defined yellow color (combination of red and green) rather than separate red and green fluorescence's. This showed that PNC-27 co-localizes with HDM-2 in the cancer cell membrane. For the control, cancer cells were incubated with FITC-labeled DO-1 (the anti-p53 antibody that recognizes the p53 12-26 sequence that is part of PNC-27). Then, confocal microscopy was used to show that there is no fluorescence on the cell membrane. This rules out the possibility that p53 also occurs in the cell membrane. Therefore the only cause for green fluorescence in cancer cells treated with PNC-27 and then DO-1 is the presence of PNC-27 in the membrane.

In a second set of experiments, we showed that we could make normal cells susceptible to PNC-27 if we induced expression of HDM-2 in their plasma membranes. The manner in which we accomplished this was to transfect a plasmid into normal MCF-10-2A breast epithelial cells that are not susceptible to PNC-27. This plasmid encoded the full length HDM-2 protein attached to a CAAX sequence (Cys-Ile-Leu-Lys) that targets newly synthesized HDM-2 to the plasma membrane. We also transfected a number of control plasmids into these cells. Overall, each plasmid had the following principal structure as shown in FIG. 11.

Figure 11:
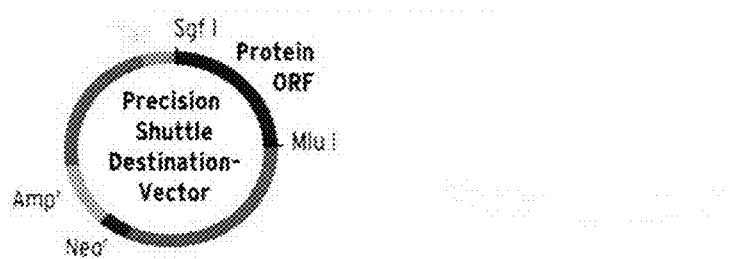
FIG. 11 depicts a schematic of the PrecisionShuttle subcloning procedure.

Referring to FIG. 11, the depiction provides a schematic of the plasmid called PrecisionShuttle for subcloning procedure is provided (obtained from OriGene, Rockville, Md.). The entry and destination vectors are digested with Sgf and Mlu I, which rarely cut in mammalian coding sequences. After a ligation reaction, the resulting clones are grown on ampicillin-containing medium to select for successful subcloning of the ORF into the destination vector. From 11:00 O'clock, going clockwise: TAG=tag protein, in this case, green fluorescent protein (GFP), Sgf1, endonuclease restriction site; protein ORF=HDM-2 sequence; MLU 1=endonuclease restriction site; the next darker gray segment is just plasmid DNA; neo=neomycin resistance gene (black); Amp'=ampicillin resistance gene (gray segment). Next is the black segment, also plasmid DNA at the end of which is the promoter that causes expression of both GFP and HDM-2 to be constitutive.

The following HDM-2 constructs were made: 1. Full length HDM-2; 2. Full length HDM-2 with the sequence Cys-Ile-Leu-Lys, (CAAX sequence) that causes the whole protein to be inserted into the cell membrane; 3. Partial length HDM-2 that lacks residues 1-109 (containing the p53- and PNC-27-binding domain), with the sequence Cys-Ile-Leu-Lys, (CAAX sequence), called del-1-109-HDM-2-CAAX that causes the whole protein to be inserted into the cell membrane; and 4. Empty vector that does not express HDM-2 at all. Based on the expression of GFP, the transfection of each of the constructs into MCF-10-2A was successful.

With the transfected constructs, two experiments were completed. The experiments included confocal microscopy measure of HDM-2 expression, pre- and post-administration of PNC-27. In the latter experiment, the cells were incubated with PNC-27. They were then incubated with a primary antibody against PNC-27, called DO-1. The cells were washed and incubated with an antibody to HDM-2. They were washed again. The cells were then incubated with fluorescent secondary antibodies to each of the primary antibodies to PNC-27 and HDM-2. The red fluorescent antibody was to PNC-27 while the green fluorescent antibody was to HDM-2. The cells were incubated with PNC-27 and tested for their viabilities using the MTT assay.

There were several possible patterns. If HDM-2 is expressed in the cell membrane and binds to PNC-27, both red and green fluorescence should appear together, which appear as visible to the observer as a yellow color. If PNC-27 inserts into the membrane and HDM-2 is expressed in the membrane, but there is no interaction (as we anticipate with del-1-109-HDM-2-CAAX), separate and distinct red and green fluorescence should be visibly observable, but no yellow fluorescence. If HDM-2 is not expressed in the cell membrane, there should be no green fluorescence in the membrane, but only inside the cell. If PNC-27 stays in the cell membrane, punctuate red fluorescence in the cell membrane should be observable.

It was found that empty vector-transfected cells had no green (HDM-2) in their membranes and very little red (PNC-27) anywhere. The transfection of the full-length construct with membrane-attaching sequence (CAAX) resulted in yellow observable in the membrane showing co-localization of PNC-27 with HDM-2. The truncated del-1-109-HDM-2-CAAX-containing cells showed separate red and green fluorescence after treatment with PNC-27 suggesting that PNC-27 does not bind to truncated HDM-2. Cells transfected with full-length HDM-2, without the membrane localization signal showed no green fluorescence (HDM-2) in the cell membrane but only in the cytosol. This illustrates that HDM-2 is not expressed in the cell membrane of normal non-cancerous cells. Red fluorescence (PNC-27) is seen in the membrane only. Thus there is no co-localization of PNC-27 and HDM-2 in the membrane (no yellow in the membrane).

Figure 12:
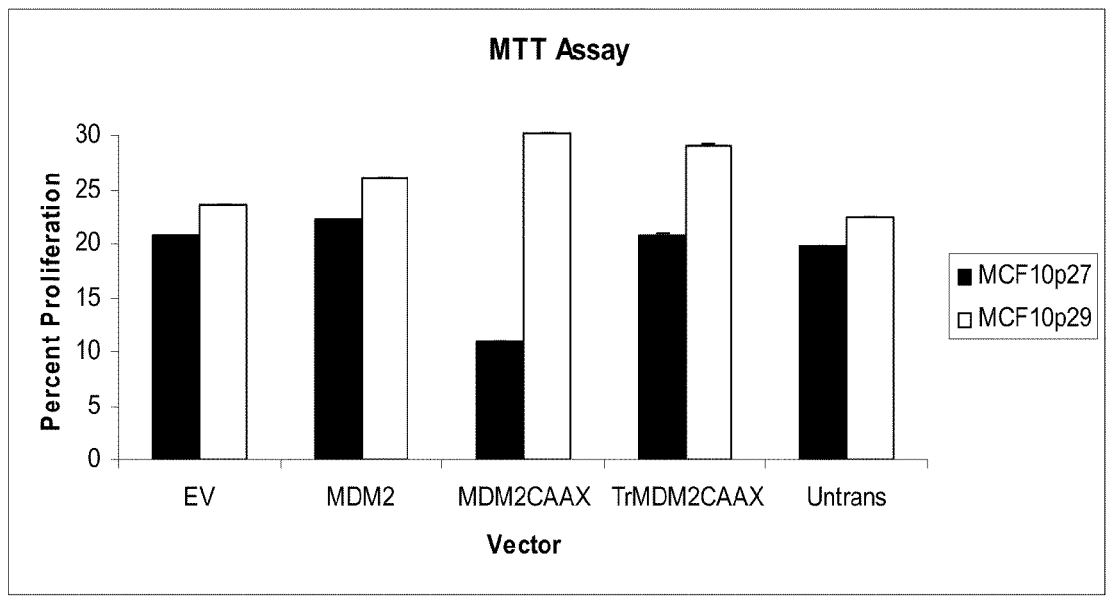
FIG. 12 depicts the experimental results of an MTT assay taken for transfection experiments.

FIG. 12 depicts the MTT assay results for cell viability for the MCF-10-2A human breast epithelial cells that have been transfected with each respective construct and then incubated with PNC-27. Each construct vector is labeled on the X-axis with the viability result (% proliferation) on the Y-axis. The dark bar-graphs are for PNC-27 experiments while the unfilled bar graphs are for a control peptide that has no effect on any cells, cancer or normal non-cancerous cells, called PNC-29. Note that cell viabilities are very similar between PNC-27- and control peptide-treated cells except for MDM-2-CAAX, which is full-length MDM-2 attached to CAAX. These cells are killed by PNC-27. These are the only cells that show that PNC-27 co-localizes with H(M)DM-2-CAAX in the cell membrane. This shows that it is HDM-2 expressed in the cancer cell membrane that is responsible for the specificity of PNC-27. Since we have shown that PNC-27 induces selective cancer cell necrosis by a mechanism that involves its binding to HDM-2 in the cancer cell membrane, PNC-27-induced cancer cell killing will be more likely show a strong dose dependence.

Figure 13:
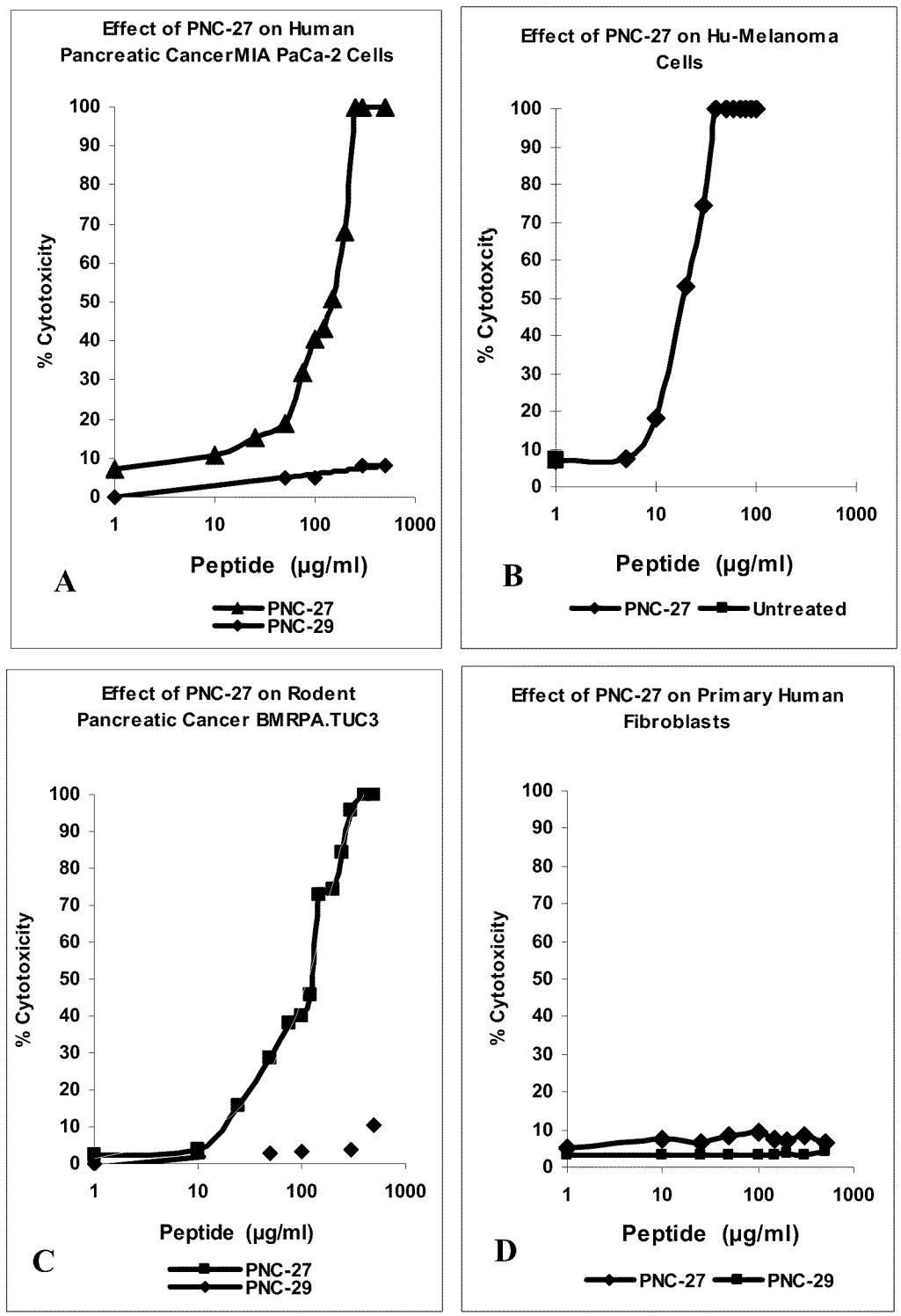
FIG. 13 graphs A through D depict the results of dose-response experiments completed on three difference cancer cell samples and in normal primary human fibroblasts to treatment in vitro with PNC-27.

FIG. 13, graphs A through D, depict the results of dose-response experiments completed on three difference cancer cell samples and one normal primary human cell line to treatment in vitro with PNC-27 (from 1-500 micrograms/ml). The cancer cell lines were human pancreatic cancer, MiaPaCa-2 (upper left, A), Hu-Melanoma cells (upper right, B), and a rodent tumor cell line, i.e., pancreatic cancer BMRPA1.TUC-3 cells (lower left, C). As controls, cells from the same cell lines were tested in parallel with a control peptide, PNC-29, over the same range of peptide concentrations. As another control, cells from primary human Ag 13145 fibroblasts (lower right, D) were treated with the same doses of PNC-27 and PNC-29, respectively.

The results are plotted along with those for PNC-29, the negative control. The results indicate that (1) there is a strong dose dependency as expected, (2) the effective range is different for different tumor cells, which have different ($LD_{50}$), (3) there is absence of any effect over the same dose range of a control peptide, and (4) PNC-27 has no effect on healthy primary human fibroblasts when used over the same dose range as applied to tumor cells. The measurements of cytotoxicity were performed by assaying for LDH in the cell supernatant.

Prototypical Small Molecules that Exhibit the Characteristics of PNC-27 that are Selectively Cytotoxic to Cancer Cells PNC-27 and PNC-28 are synthetic peptides which include an HDM-2 binding region and a membrane resident peptide. Various tests and experimentation completed by the present inventors have led the inventors to the surprising discovery that not only peptide, but also combined peptide and non-peptide, as well as wholly non-peptide materials may be constructed to exhibit and induce selective and specific cancer cell-necrosis, while leaving normal non-cancerous cells unaffected.

Once the present inventors surprisingly determined the role of each component of the synthetic peptide molecules, it became possible to design additional molecules based on the discoveries of the proposed mechanism of action. Because peptide-based materials are characteristically non-rigid, the synthetic peptides employed with the methods of the present invention may require some time in order to adopt the proper conformation before they can bind to their desired target (here, HDM-2). Also, compositions that are not wholly composed of peptides may exhibit longer half lives, upon administration to a plurality of cancer cells or in vivo after administration to a living organism with cancer.

Further, the size of newly designed compositions are in accordance with the tested synthetic peptides, as sizes shorter than 32 AA can typically be administered to a living organism while rarely triggering an immune response.

As such, hybrid materials containing peptide and non-peptide components, along with wholly non-peptide materials may be used with the methods of the present invention. The synthesis of one or more of the compounds may be subsequently followed by purification, as is commonly done in the art. The compounds synthesized are preferably in purified form to be used as the compound and with the methods of the present invention.

Purified form, as used herein, generally refers to material which has been isolated under certain desirable conditions that reduce or eliminate unrelated materials, i.e. contaminants. Substantially free from contaminants generally refers to free from contaminants within analytical testing and administration of the material. Preferably, purified material is substantially free of contaminants is at least 50% pure, more preferably, at least 90% pure, and more preferably still at least 99% pure. Purity can be evaluated by conventional means, e.g. chromatography, gel electrophoresis, immunoassay, composition analysis, biological assay, NMR, and other methods known in the art.

It should be noted that though the below-referenced experiments have not yet been completed on the other compounds useable with the methods of the present invention, the inventors contemplate similar results as obtained herein, based on the characteristics of the various components of the compounds, in combination with the proposed and verified mechanism of action.

TABLE I

Compositions of the Present Invention and Employable with the Methods of the Present Invention

| No | HDM-2 binding component | Membrane Resident Component | Name |
|---|---|---|---|
| 1 | 12-26 p53 protein, residues (PPLSQETFSDLWKLL) (SEQ ID NO: 1) | KKWKMRRNQFWVKVQRG (SEQ ID NO: 3) | PNC-27 |
| 2 | 17-26 p53 protein, residues (ETFSDLWKLL) (SEQ ID NO: 2) | KKWKMRRNQFWVKVQRG (SEQ ID NO: 3) | PNC-28 |
| 3 | 12-26 p53 protein, residues (P*P*LSQETFSDLWKLL) (SEQ ID NO: 1), where * denotes D-amino acid, rather than natural, L-amino acid (D & L are optical isomers) | KKWKMRRNQFWVKVQRG (SEQ ID NO: 3) | PNC-27-D amino acid |
| 4 | 12-26 p53 protein, residues (PPLSQETFSDLWKLL) (SEQ ID NO: 1) | KKWKMRRNQFWVKVQRG-LLR (SEQ ID NO: 3) | PNC-27-leupeptin |
| 5 | 17-26 p53 protein, residues (ETFSDLWKLL) (SEQ ID NO: 2) | KKWKMRRNQFWVKVQRG-LLR (SEQ ID NO: 3) | PNC-28-leupeptin |
| 6 | 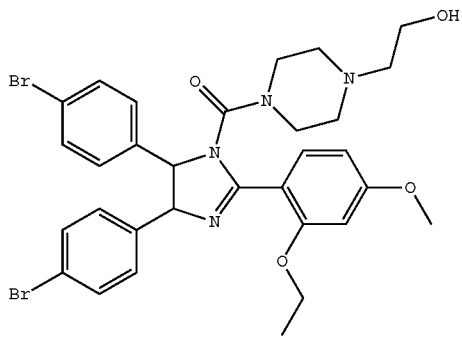 Nutlin-2 | KKWKMRRNQFWVKVQRG (SEQ ID NO: 3) | Nutlin-2-MRP |
| 7 | 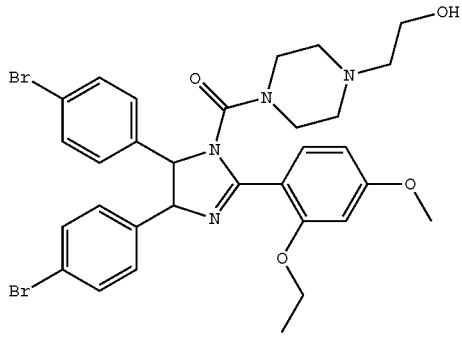 Nutlin-2 | Guanidinylated biphenyl (structure shown below) | Nutlin-2-guanidinylated biphenyl |

TABLE I-continued

Compositions of the Present Invention and Employable with the Methods of the Present Invention

| No | HDM-2 binding component | Membrane Resident Component | Name |
|---|---|---|---|
| 8 | 12-26 p53 protein, residues (PPLSQETFSDLWKLL) (SEQ ID NO: 1) | Guanidinylated biphenyl (structure shown below) | p5312-26 guanidinylated biphyenls |
| 9 | XFMXXXEXLX (SEQ ID NO: 10), where X in first position is actyl moiety (CHO), X in fourth position is alpha-amino isobutyric acid, X in fifth position is phosphonomethyl-phenylalanine, X in sixth position is 6-chlorotryptophan, X in eighth position is 1-amino-cyclopropanecarboxylic acid, X in tenth position is NH2. | KKWKMRRNQFWVKVQRG (SEQ ID NO: 3) | Non-native p53-MRP |

TABLE II

SEQUENCE ID NOS:

| SEQUENCE ID NO. | SEQUENCE | Name |
|---|---|---|
| SEQ ID NO: 1 | PPLSQETFSDLWKLL | Residues 12-26 p53, MDM-2 binding domain |
| SEQ ID NO: 2 | ETFSDLWKLL | Residues 17-26 p53, MDM-2 binding domain |
| SEQ ID NO: 3 | KKWKMRRNQFWVKVQRG | Membrane resident peptide (MRP), Antennapedia |
| SEQ ID NO: 4 | MPFSTGKRIMLGE | Sequence from cytochrome P450, used as a control |
| SEQ ID NO: 5 | PPLSQETFSDLWKLLKKWKMRRNQFWVKVQRG | PNC-27 |
| SEQ ID NO: 6 | ETFSDLWKLLKKWKMRRNQFWVKVQRG | PNC-28 |
| SEQ ID NO: 7 | MPFSTGKRIMLGEKKWKMRRNQFWVKVQRG | PNC-29 (Control Peptide) |
| SEQ ID NO: 8 | PPLSQETFSDLWKLLKKWKMRRNQFWVKVQRGLLRX, where X is acetyl moiety | PNC-27-Leupeptin |
| SEQ ID NO: 9 | ETFSDLWKLLKKWKMRRNQFWVKVQRGLLRX, where X is Acetyl moiety, CHO | PNC-28-Leupeptin |
| SEQ ID NO: 10 | XFMXXXEXLX, where X in first position is actyl moiety (CHO), X in fourth position is alpha-amino-isobutyric acid, X in fifth position is phosphonomethyl-phenylalanine, X in sixth position is 6-chlorotryptophan, X in eighth position is 1-amino-cyclopropane-carboxylic acid, X in tenth position is NH2. | Non-native p53 [Ac-Phe-Met-Aib-pmp-6-Cl-Trp-Glu-Ac₃c-Leu-NH₂, where Aib = alpha-amino-isobutyric acid, pmp = phosphonomethyl-phenylalanine, 6-Cl-Trp = 6-chlorotryptophan, Ac₃c = 1-amino-cyclopropane-carboxylic acid.] |
| SEQ ID NO: 11 | LLRX, where X is acetyl moiety, CHO | Leupeptin |

PNC-27-D Amino Acid

In order to slow the degradation of the PNC-27 synthetic peptide in situ, it may be desirable to attach a D-amino acid to the p53 part of the protein. The D-amino acid may be inserted into the peptide chain, or preferably exchanged, such that one of the existing amino acids may take the form of its optical isomer, 'D' form, over the naturally occurring form. The 'D' amino acid may be part of the originally synthesized peptide. Preferably, this may be an amino acid towards the amino terminal end. This may best be accomplished by adding one amino acid on the amino terminus of the peptide, e.g., D-alanine. The D amino acid may be synthetically placed on the synthetic peptides through the use of methods known to those skilled in the art. The conformation and helicity of the synthetic peptide with at least one D-amino acid added to the amino terminus of the parent peptide is not expected to disrupt the active three-dimensional structure of the peptide. This can be confirmed in solution studies such as by Nuclear Magnetic Resonance (NMR).

PNC-27-Leupeptin or PNC-28-Leupeptin

In order to lengthen the half life of the synthetic peptide material, leupeptin (N-acetyl-L-leucyl-L-leucyl-L-argininal) (LLRX, where X is the acetyl moiety) (SEQ ID NO:11), a well-known protease inhibitor may be attached to the synthetic peptide. As both PNC-27 and PNC-28 are small peptides, upon administration they may be quickly catabolized or degraded by extra- and intracellular proteases. Thus, methods known to those skilled in the art may be used to attach leupeptin, a known protease inhibitor, with capabilities to inhibit a broad spectrum of proteases, onto the synthetic peptides. For example, leupeptin may be synthesized onto the end of the MRP by solid state synthesis, a common method for creating synthetic proteins. Also, leupeptin may be chemically added onto the carboxyl terminal end of the MRP by conventional chemical means, as known to those skilled in the art.

Preferably, the leupeptin is attached to the membrane resident peptide in such a manner that once the MRP is inserted into the cancer cell membrane, the leupeptin is able to disassociate and inhibit protease activity inside and outside the cell. Alternatively, leupeptin may remain attached and may bind to nearby proteases, blocking their degradation of the peptide. Thus, leupeptin may desirably be split off from MRP to inhibit protease in the cell. Thus, the synthetic peptide PNC-27 or PNC-28, with leupeptin attached to the carboxyl terminal end of the MRP will likely considerably lengthen the life span of the synthetic peptide in situ.

It is desired that leupeptin is attached to or towards the carboxyl terminal end of the membrane resident component. Attachment to the carboxyl rather than the amino terminal end is due to the fact that the arginine residue must be maintained in the aldehyde state; as oxidation to the carboxyl oxidation state results in inactivity. Also with leupeptin on the carboxyl terminus, no serious impact to the three dimensional structure of the overall peptide is contemplated to be created. In fact, since it is positively charged, it will likely further stabilize the desired alpha-helical conformation of the MRP and of the HDM-2 binding component. The addition of leupeptin to PNC-27 or PNC-28 is believed to maintain the conformation of the MRP while increasing the half life of the synthetic peptide material. Thus, the compound (PNC-27 or PNC-28, with leupeptin attached to its carboxyl terminal end) may remain active in the body of the subject for a longer period of time. It should be noted that since leupeptin is a small peptide composed of three amino acids (leucine-leucine-arginine), the addition of leupeptin onto the carboxyl terminal end of the MRP will likely not greatly increase the size of the synthetic peptide.

Methods known and used by those skilled in the art, including NMR, spectroscopy, and/or computational modeling, may be used to analyze and confirm the structure and effects of the synthetic peptide attached to leupeptin. For a detailed discussion of leupeptin and the family of similar small molecule enzyme (protease) inhibitors which may be likewise incorporated as compounds employable with the present invention, the following publications are provided:
Moldoveanu, T., et al., Crystal Structures of Calpain-E64 and -Leupeptin Inhibitor Complexes Reveal mobile Loops Gating the Active Site, J. Mol. Biol. (2004) 343, 1313-1326 (doi:10.1016/j.jmb.2004.09.016); and
Rohr, K. et al., X-ray. Structures of Free and Leupeptin-complexed Human αI-Tryptase Mutants: indication for an α→β-Tryptase Transition, J. Mol. Biol. (2006)357, 195-209 (doi:10.1016/j.jmb.2005.12.037). The aforementioned publications are incorporated herein by reference in their entireties.

Nutlin-2-MRP

Nutlins are known to those in the art as small molecule compounds shown to have an MDM-2 binding affinity. Structure, uses, and characteristics of Nutlins are known by those in the art and are disclosed and described in several references, including:
Vassilev, L. T., et al., In-Vivo Activation of the p53 Pathway by Small-Molecule Antagonists of MDM-2, SCIENCE, v. 303, 6 Feb. 2004, 844-848 (www.sciencemag.org); and
Vassilev, L. T., et al, Selective small-molecule inhibitor reveals critical mitotic functions of human CDK1, PNAS, v. 103, No. 28, Jul. 11, 2006, 10660-10665. The contents of both of these articles are incorporated herein by reference. Nutlins act on cancer cells to block the p53-hdm-2 interaction. Nutlins come in three different forms, nutlin-1, nutlin-2, and nutlin-3. However, for the purposes of this invention, nutlin-2 may be employed. Its structure is shown below.

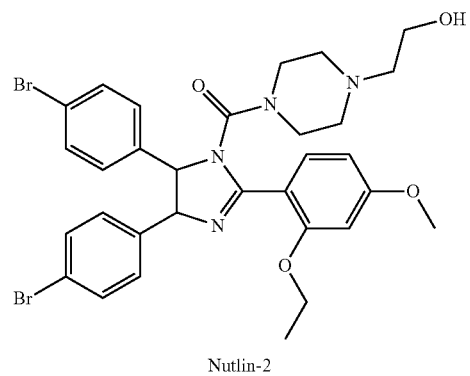 [SMILES: CCOc1cc(OC)ccc1C1=NC(c2ccc(Br)cc2)C(c2ccc(Br)cc2)N1C(=O)N1CCN(CCO)CC1]

Nutlin-2

Preferably, the inventors of the present invention attach nutlin-2 to the amino terminal end of the membrane resident peptide (MRP) to create a compound of the present invention and which may be administered in accordance with the methods 100, 200, 300 of the present invention. Nutlin-2 contains a desirable reactive group, i.e., the —CH$_2$OH group, which may be the site for further chemistry to attach the nutlin-2 to the MRP.

In this case, nutlin-2 is esterified to the side chain —COOH group of terminally blocked aspartic acid; this becomes the first modified amino acid in the MRP. The nutlin-2 component has a known MDM-2/HDM-2 binding affinity, while the membrane resident component has a membrane active character which is disclosed and described herein.

Nutlin-2-Guanidinylated Biphenyl

Small molecule carriers are known by those skilled in the art, and are disclosed and described in the publication: Okuyama, M. and Laman, H. and Kingsbury, S. R. and Visintin, C. and Leo, E. and Edward, K. L. and Stoeber, K. and Boshoff, C. and Williams, G. H. and Selwood, D. L. Small-molecule mimics of an α-helix for efficient transport of proteins into cells. Nature Methods, 4 (2). pp. 153-159 (2007). ISSN 15487091, which is incorporated by reference herein in its entirety.

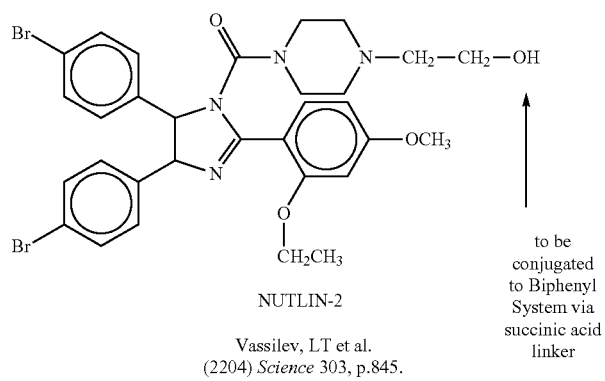
NUTLIN-2
Vassilev, LT et al.
(2204) *Science* 303, p.845.
to be
conjugated
to Biphenyl
System via
succinic acid
linker
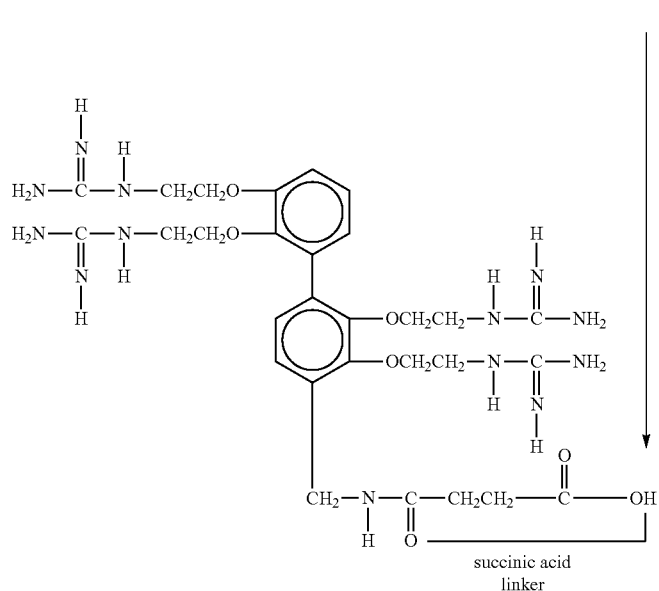
Biphenyl System
Okuyama, M., et al., *Nature Methods*, published on-line
January 2007.

-continued

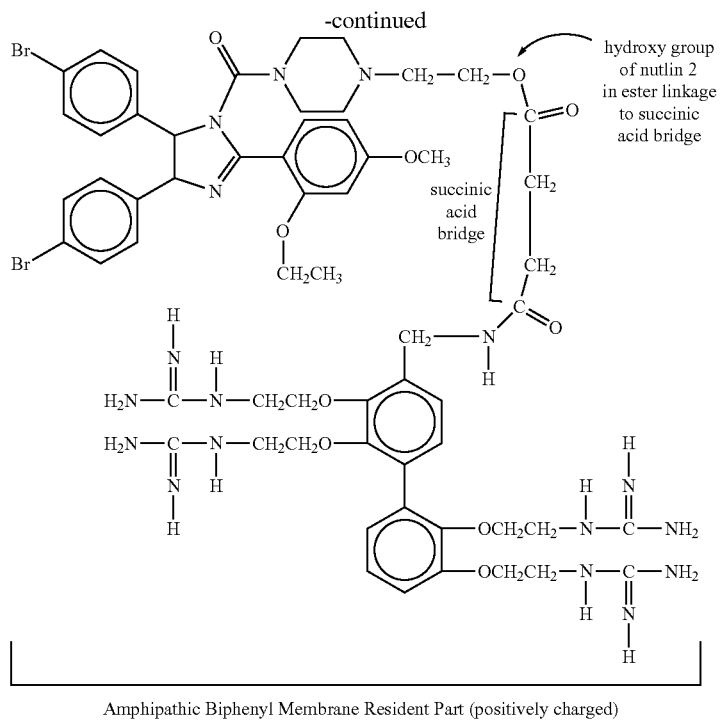

Amphipathic Biphenyl Membrane Resident Part (positively charged)

NUTLIN-2
Binds HDM-2

The nutlin-2-guanidinylated biphenyl compound may be used as the anti-cancer compound or with one or more of the methods 100, 200, 300 of the present invention in order to cause membranolysis in cancer cells. As a non-peptide peptidomimetic agent, this compound may exhibit a longer half-life than the synthetic peptide materials when administered to a subject or to a plurality of cells in situ.

The biphenyls were designed to contain a reactive amino group to which a succinic acid moiety was attached, leaving a very reactive —COOH group that allows attachment of a wide variety of compounds. Nutlin-2 is ideal in that it has a reactive —CH2OH group as shown in the two figures above. This can readily be esterified to the —COOH of the succinate moiety of the guanidinylated biphenyl.

Certain experiments may be desirably completed on the synthetic non-peptide nutlin-2-guanidinylated biphenyl material in order to analyze and confirm its characteristics as an anti-cancer activity. For example, one million cancer cells are to be incubated with a dose range of the new compound (nutlin-2-guanidinylated biphenyl) from 10 nM to 100 uM and cell viability may be analyzed (as set forth for the PNC-27 and PNC-28 peptides above) using trypan blue exclusion and MTT assay, analyzed for the release of LDH into the medium, and analyzed for caspase-3 (for possible apoptosis).

In the in vitro experiments with PNC-27 and PNC-28, the peptides were added with new medium every one-two days at the specified dose when total cell killing occurs over several days. When the cancer cells are treated with a peptidomimetic, it will not be necessary to add more compound periodically because the half-life of the peptidomimetic is proposed to be much greater than for the parent peptide. The inventors expect with the aforementioned experiments, that the medium will not need to be changed to incorporate additional compound. Thus, one dose of the peptidomimetic may be sufficient total cancer cell killing.

P53-12-26-Guanidinylated Biphenols

Another compound of the present invention includes the p53 12-26 residues chemically bound to the guanidinylated biphenyl material, previously disclosed and described above. In order to attach the guanidinylated biphenyl to the HDM-2 binding component (residues 12-26 of p53), the inventors of the present invention will take terminally blocked serine and react it with an activator of its side chain-OH group. Next, the inventors will add the biphenyl, which contains the succinic acid moiety. This will form a covalent ester bond with terminally blocked serine. Then, this modified terminally blocked serine will be added to the solid-phase synthesized p53 residues 12-26, to add it onto the activated carboxyl terminal end of this peptide on the solid phase column. This will give us p53 12-26 peptide linked to guanidinylatedbiphenyl-serine. The synthesized guanidinylated biphenyls attached to the carboxyl terminal end of the MDM-2 binding domain (p53 residues 12-26) may exhibit a longer half life than the purely peptide materials as this compound lacks the MRP peptide residues that can be hydrolyzed. Also the presence of the "abnormal" carboxyl terminal serine may inhibit peptidases. This may also contribute to a lower $IC_{50}$ for this compound as compared to the purely peptide materials, PNC-27 and PNC-28.

The fact that we have a helical, positively charged moiety on the carboxyl terminal end of the p53 12-26 sequence makes it very likely that this hybrid molecule will be very active, so it will bind to hdm-2 while the non-peptide biphenyl moiety will may it amphipathic, membrane active and allow pore formation. In order to further analyze and verify the structure of the compound, molecular modeling and/or multi-dimensional NMR studies in solution may be completed.

Non-Native p53-MRP

Non-native p53, as referred to herein, refers to Ac-Phe-Met-Aib-pmp-6-Cl-Trp-Glu-Ac$_3$c-Leu-NH$_2$ (SEQ ID NO: 10), Where Aib=alpha-amino-isobutyric acid, pmp=phosphonomethyl-phenylalanine, 6-Cl-Trp=6-chlorotryptophan, Ac$_3$c=1-amino-cyclopropanecarboxylic acid (XFMXXXEXLX, where X in first position is actyl moiety (CHO), X in fourth position is alpha-amino-isobutyric acid, X in fifth position is phosphonomethyl-phenylalanine, X in sixth position is 6-chlorotryptophan, X in eighth position is 1-amino-cyclopropanecarboxylic acid, X in tenth position is NH2). The synthesis and structure of this compound is known to those skilled in the art, as it is publicly available in the publications: Chene, P. et al (2000) J. Mol. Biol.; Chene, P. et al (2002) FEBS Lett. 529, 293-297. In these references, non-native p53 materials were used for blocking the binding of p53 to HDM-2 in cancer cells. In furtherance to the compound and methods 100, 200, 300 of the present invention, non-native p53 may be attached to the MRP through straight solid phase synthesis, as is known to those skilled in the art. Similarly, a chemical complexing step may be completed in order to bind the non-native p53 to the MRP. In the case of the unnatural amino acids, since the carboxyl terminal residue is a leucine, a fusion of the unnatural sequence to amino terminal activated MRP can be performed.

The terms used in this specification generally have their ordinary meanings in the art, within the context of this invention and in the specific context where each term is used. Certain terms are discussed below, or else where in the specification, to provide additional guidelines to the practitioner in describing the compositions and methods of the invention, as well as how to make and use them.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. Patents, patent application, publications, products descriptions, and protocols are cited throughout this application, the disclosures of which are incorporated herein by reference in their entries for all purposes.

Experimental Protocol:

The following provides a discussion of the experimental methods employed for various experimental results described herein.

Confocal Microscopy:

Cells were released with trypsin from their TCFs and grown on glass cover slips in 24-well dishes until they reached 50-60% density. After removal of the spent medium and PBS washing buffer they were treated for up to 15 min at 37° C. in a humidified 5% CO$_2$-95% air incubator chamber with PNC-27 or PNC-29 (control) at 50 µg/ml incubation medium. At the end of the incubation the cells were washed and fixed in 3% paraformaldehyde in PBS (pH 7.2) supplemented with 0.01% glutaraldehyde for 1.5 h followed by extensive washing and transfer into PBS for storage until mounting on glass slides for microscopy. Free aldehyde groups were quenched by incubating cells with glycine and sodium borohydride (NaBH$_4$), followed by washing in PBS. Cells were then stained (direct staining) for 2 h, 4° C., with fluorescein-labeled mouse monoclonal antibody against p53 [FITC-mAbα-p53 (DO-1)] (5 µg/ml) and rhodamine-labeled (TRITC-) mAbα-against H/R/MDM-2 (5 µg/ml). After removal of non-reactive Ab and extensive washing, the cover slips were mounted over antifade (Molecular Probes—Invitrogen, CA) on glass slides and examined with a laser-equipped Olympus Confocal microscope 1×76. Results were digitally recorded. The co-localization of the two Abs was confirmed by overlapping green (anti-p53) and red (anti-H/R/MDM-2) fluorescent labels which produced a yellow color.

Transmission Electron Microscopy:

The following is the experimental protocol for the TEM picture shown in FIG. 6. Cells (2×10$^6$) were grown in 75 cm$^2$ TCFs until ~80% confluency when they were placed on ice, washed with ice cold PBS, scraped and collected in PBS, and centrifuged at 500×g, for 10 min and at 50° C. After removal of the supernatant the cell pellet was resuspended in homogenization buffer [0.022M Na—PO$_4$, pH7.4, 0.001M MgCl$_2$, 0.25M sucrose, cocktail of protease inhibitors (Pierce)] and homogenized on ice in a tissue homogenizer (Omni International). The homogenate was centrifuged at 1000×g, 5° C., for 10 min when pellet and supernatant were separately collected. The supernatant was centrifuged for 1 h in a SW55 rotor at 140,000×g, 6° C. (Beckman LB80M Ultracentrifuge) and the pellet of this centrifugation was resuspended in ice cold PBS. The resuspended pellet was re-centrifuged for 30 min at 30,000×g, 6° C. The supernatant was removed and the pellet was dissolved in solubilization buffer (1% Triton X-100 in 0.06M Tris-HCl, pH7.5, 0.001M Na-orthovanadate, 0.015M MgCl$_2$, cocktail of protease inhibitors) for subsequent protein measurements, sododecylsulfate polyacrylamide gel electrophoresis (SDS-PAGE) followed by staining and immunoblotting as described below for FIG. 7. Prior to solubilization of the 30,000×g pellet a small amount was removed mechanically from the pellet, transferred and fixed in 2.5% glutaraldehyde in 0.113M Cacodylate buffer (pH7.4). After overnight fixation, the protein sample was processed through uranylacetate and osmium staining and embedded in Epon for TEM as described (Pytowsky et al., J Exp Med 167:421-439, 1988). Sections (60 nm) were examined and recorded in a Zeiss EM10. Photographs shown were taken at Magn. ×85,000.

Western Blot:

These procedures were used to obtain the data presented in FIG. 7. Cells (2×10$^6$) were grown in 75 cm$^2$ TCFs until ~80% confluency when they were placed on ice, washed with ice cold PBS, scraped and collected in PBS. The collected cell volume was divided into two equal parts. One part was used to obtain whole cell lysates while the second part was used to prepare purified plasma membrane as described above and briefly summarized as follows: To obtain purified plasma membrane, the cells were centrifuged at 500×g, for 10 min and at 5° C. After removal of the supernatant the cell pellet was resuspended in homogenization buffer [0.022M Na—PO$_4$, pH7.4, 0.001M MgCl$_2$, 0.25M sucrose, cocktail of protease inhibitors (Pierce)] and homogenized on ice in a tissue homogenizer (Omni International). The homogenate was centrifuged at 1000×g, 5° C., for 10 min when pellet and supernatant were separately collected. The supernatant was centrifuged for 1 h in a SW55 rotor at 140,000×g, 6° C. (Beckman LB80M Ultracentrifuge) and the pellet of this centrifugation was resuspended in ice cold PBS. The resuspended pellet was re-centrifuged for 30 min at 30,000×g, 6° C. The supernatant was removed and the pellet was dissolved in solubilization buffer (1% Triton X-100 in 0.06M Tris-HCl, pH7.5, 0.001M Na-Orthovanadate, 0.015M MgCl$_2$, cocktail of protease inhibitors) for subsequent protein measurements, sododecylsulfate polyacrylamide gel electrophoresis (SDS-PAGE) followed by staining and immunoblotting as described below.

To obtain whole cell lysates, the cells in PBS were pelleted for 10 min at 250×g and 5° C., the supernatant was removed and the pellet resuspended in lysing buffer (2% Triton X-100 in 0.06M Tris-HCl, pH7.5, 0.001M Na-orthovanadate, cocktail of protease inhibitors). The protein concentration was measured in the total cell lysates as well as the plasma membrane preparations. Equal amounts of proteins were prepared with 2× Laemmli Sample Buffer under reducing conditions (5% 2-beta mercaptoethanol, boiling for 3 min) and separated in linear 12% SDS-PAGE gels, electrophoretically transferred to nitrocellulose paper for immunoblotting with antibodies (each at 0.005 mg/ml blocking buffer) to MDM-2, HDM-2 and p53. It should be noted, that the preparation of the total cell lysates and the lysates of the cells' plasma membrane for the two immunoblots followed exactly the procedure described above. After electrophoretic transfer of the separated polypeptides, the remaining charged sites of the nitrocellulose membrane were then blocked 2×30 min at RT with 5% dry milk in TBS-T buffer, washed with dH$_2$O and incubated for 1 h at Room Temperature (RT) with the primary antibody solution (MDM-2, HDM-2, p53). The membrane was then washed extensively with TBS-T and reincubated for 30 min, RT, with the secondary antibody solution of HRP-conjugated Donkey-anti-Mouse IgG (HRP-D anti-M IgG) 1:1000 in 0.1% milk in TBS-T). After extensive washing in TBS-T buffer followed by dH$_2$O to remove non-reactants, Immun-Star HRP Peroxide Buffer+Immun-Star HRP Luminol/Enhancer (ratio 1:1) was added to the nitrocellulose membranes and the chemiluminescent reaction was exposed in complete darkness to X-ray film. Exposure time was 10 min.

Transmission Electron Microscopy:

Cells (1×10$^6$) were grown in 6-well dishes overnight then spent medium was removed, the cells were washed with PBS and treated at 37° C. with PNC-28 at 50 μg/ml in PBS. At different time points (5-30 min) during the PNC-28 treatment the cells were washed and fixed in 3% buffered paraformaldehyde supplemented with 0.01% glutaraldehyde for 1.5 h. After extensive washing, the cells were treated with glycine and NaBH$_4$ as described above followed by 3 times washing in PBS. The cells were then post-fixed in 1% glutaraldehyde in cacodylate buffer (0.113M, pH7.2) overnight, at which time they were scraped into PBS and centrifuged into a pellet. The cells were washed in cacodylate buffer and once more post-fixed and stained in 1% osmium tetraoxide for 1 h, rt. The fixed cells were dehydrated through sequential passages in increasing concentrations of ethanol and embedded in agar which was then exchanged for Epon. After hardening the Epon for 72 h, thin sections (60 nm) were cut on an ultramicrotome, stained with uranyl acetate and examined in a Zeiss. EM10 transmission electron microscope.

Scanning Electron Microscopy:

Cells (3×10$^4$) were grown on glass cover slips and treated with PNC-27 (50 μg/ml) for 3 minutes. Cells were then fixed in 3% buffered paraformaldehyde supplemented with 0.01% glutaraldehyde for 1.5 h. After initial fixation, cover slips were rinsed several times with PBS for a minimum of 15 minutes, followed by post fixation with 1% osmium tetroxide in 0.1M phosphate buffer, pH 7.4, for 1 hour. Cover slips were then dehydrated using a series of graded ethyl alcohols (70% for 15 min, 95% for 15 min. and 3 changes of 100% for 10 min. each). Cover slips were then mounted on metal stubs, platinum sputter-coated and viewed using a LEO 1550 scanning electron microscope.

Dose Response Experiments:

For the dose response experiments (n=3-5), 0.1 ml of each of the cells (70,000 cells/ml of culture medium) were seeded into each of the wells of 96-well TCD (7000 cells/well) and allowed to adhere overnight. On the next day, the medium was removed and 0.1 ml of the different PNC-27 concentrations in PBS (37° C.) was added to triplicate wells and incubation continued for 30 min at 37° C. At t=0 min and t=30 min a triplicate set of supernatants and cell lysates were removed that had been incubated in PBS only. These two sets of samples were used to establish background values for LDH release and LDH content of cells incubated for 0 and 30 min, respectively, in PBS only. At the end of the incubation period 0.05 ml of culture supernatant were removed, and 0.05 ml of lysis buffer (2% Triton-X-100 in dH$_2$O) were added to each well to obtain cell lysis and the release of cell-contained LDH. For the measurement of the LDH activities present in the cell supernatants and the cell lysates, 0.05 ml from each sample were mixed with 0.05 ml of the substrate mix (CytoTox 96 Non-radioactive Cytotoxicity Assay, Promega, Corp, Madison, Wis.) incubated in the dark and at room temperature for 30 min, when 0.05 ml of stop solution was added. The results were read at OD$_{490\ nm}$ in an ELISA plate reader within 15 min of stopping the color development in the wells. The results were calculated as advised by the manufacturers guidelines (CytoTox 96 Non-radioactive Cytotoxicity Assay, Promega), and the data were expressed in % Cytotoxicity. Since for each dose (triplicate measurements), the values calculated for SEM were ±<5% of the results shown, they do not appear in the computer-drawn graphs.

What is claimed is:

1. A method of treating cancer in a subject, said method comprising:

providing a subject having a plurality of cancer cells; and administering to the subject, a therapeutically effective amount of a composition including:

an HDM-2 binding component comprising:

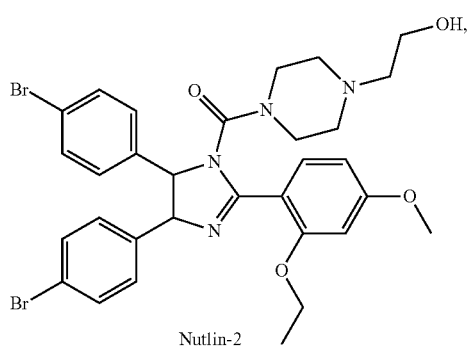 [SMILES: CCOc1cc(OC)ccc1C1=NC(c2ccc(Br)cc2)C(c2ccc(Br)cc2)N1C(=O)N1CCN(CCO)CC1]
   Nutlin-2 and a membrane resident component comprising:

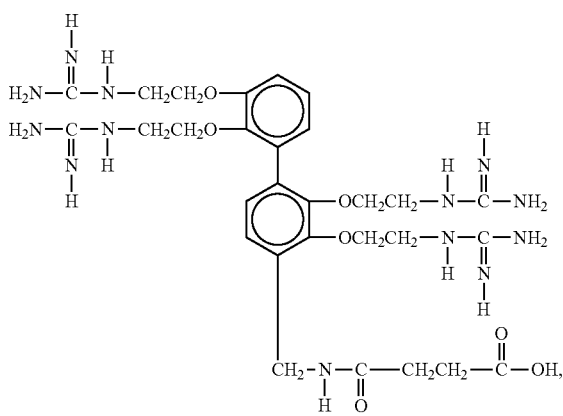

said membrane resident component bound to said HDM-2 binding component.

2. The method of claim 1, further comprising the step of observing necrosis in the cancer cells.

3. The method of claim 1, whereby the cancer cells are necrosed.

* * * * *